(12) United States Patent
Potter et al.

(10) Patent No.: US 9,861,738 B2
(45) Date of Patent: Jan. 9, 2018

(54) FLEX TIP FLUID LUMEN ASSEMBLY WITH TERMINATION TUBE

(71) Applicant: St. Jude Medical, Cardiology Division, Inc., St. Paul, MN (US)

(72) Inventors: Daniel Joe Potter, Stillwater, MN (US); Xuan Yen Khieu, Maple Grove, MN (US); Benjamin Carl Breidall, Eden Prairie, MN (US); Andrew Oliverius, Eagan, MN (US); Sameer Deviprasad Pai, Plymouth, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 407 days.

(21) Appl. No.: 14/213,289

(22) Filed: Mar. 14, 2014

(65) Prior Publication Data

US 2014/0200441 A1 Jul. 17, 2014

Related U.S. Application Data

(63) Continuation-in-part of application No. 13/838,124, filed on Mar. 15, 2013, now Pat. No. 8,814,825.

(Continued)

(51) Int. Cl.
*A61M 3/02* (2006.01)
*A61B 5/01* (2006.01)
(Continued)

(52) U.S. Cl.
CPC ............ *A61M 3/0279* (2013.01); *A61B 5/01* (2013.01); *A61B 5/065* (2013.01); *A61B 18/1492* (2013.01); *A61M 25/0136* (2013.01); *A61M 25/0144* (2013.01); *A61M 25/0147* (2013.01); *A61B 18/02* (2013.01);
(Continued)

(58) Field of Classification Search
CPC .......... A61B 18/1492; A61B 2218/002; A61B 2018/00577; A61M 25/0138; A61M 2025/0166
See application file for complete search history.

(56) References Cited

U.S. PATENT DOCUMENTS 7,815,635 B2 10/2010 Wittkampf et al.
7,857,810 B2 * 12/2010 Wang .................. A61B 18/148
606/41

(Continued)

FOREIGN PATENT DOCUMENTS

CN 101528145 A 9/2009
CN 101708130 A 5/2010
(Continued)

*Primary Examiner* — Aarti B Berdichevsky
(74) *Attorney, Agent, or Firm* — Dykema Gossett PLLC

(57) ABSTRACT

A catheter tip is disclosed comprising a tip electrode comprising a ledge feature, and a center cavity and a manifold assembly comprising a fluid lumen manifold and a stop tube. The stop tube can be coupled to the fluid lumen manifold and configured to abut the ledge feature such that a distal end of the fluid lumen manifold extends a pre-determined distance into the center cavity of the tip electrode. The fluid lumen manifold can comprise a plurality of sideholes which can be sized and configured to distribute an irrigant to the tip electrode. The catheter tip can comprise a flexible tip electrode.

19 Claims, 22 Drawing Sheets

Related U.S. Application Data

(60) Provisional application No. 61/643,748, filed on May 7, 2012, provisional application No. 61/820,518, filed on May 7, 2013.

(51) Int. Cl.
  *A61B 5/06* (2006.01)
  *A61M 25/01* (2006.01)
  *A61B 18/14* (2006.01)
  *A61M 25/00* (2006.01)
  *A61B 18/02* (2006.01)
  *A61B 18/18* (2006.01)
  *A61B 18/22* (2006.01)
  *A61B 18/00* (2006.01)
  *A61B 34/20* (2016.01)

(52) U.S. Cl.
  CPC ......... *A61B 18/1815* (2013.01); *A61B 18/22* (2013.01); *A61B 2018/00357* (2013.01); *A61B 2018/00577* (2013.01); *A61B 2018/00815* (2013.01); *A61B 2018/00821* (2013.01); *A61B 2018/00839* (2013.01); *A61B 2034/2046* (2016.02); *A61B 2217/007* (2013.01); *A61B 2218/002* (2013.01); *A61M 25/007* (2013.01); *A61M 2025/0059* (2013.01); *A61M 2025/015* (2013.01)

(56) References Cited

U.S. PATENT DOCUMENTS

| | | | |
|---|---|---|---|
| 7,998,141 B2 | 8/2011 | Wittkampf et al. | |
| 8,016,784 B1 * | 9/2011 | Hayzelden | A61M 25/0012 604/104 |
| 8,162,934 B2 * | 4/2012 | Potter | A61B 18/1492 604/95.04 |
| 8,187,267 B2 | 5/2012 | Pappone et al. | |
| 8,206,404 B2 | 6/2012 | de la Rama et al. | |
| 8,287,533 B2 | 10/2012 | Wittkampf et al. | |
| 8,374,670 B2 * | 2/2013 | Selkee | A61B 5/6885 600/374 |
| 8,480,669 B2 | 7/2013 | Pappone et al. | |
| 8,715,279 B2 | 5/2014 | de la Rama et al. | |
| 8,734,440 B2 | 5/2014 | Wu | |
| 8,790,341 B2 | 7/2014 | Pappone et al. | |
| 8,827,910 B2 | 9/2014 | de la Rama et al. | |
| 8,979,837 B2 * | 3/2015 | de la Rama | A61M 25/007 606/41 |
| 2002/0165461 A1 | 11/2002 | Hayzelden et al. | |
| 2005/0070844 A1 * | 3/2005 | Chow | A61M 25/0012 604/95.04 |
| 2005/0070894 A1 | 3/2005 | McClurken | |
| 2006/0264820 A1 | 11/2006 | Ponzi et al. | |
| 2007/0270679 A1 * | 11/2007 | Nguyen | A61M 25/0043 600/373 |
| 2007/0270791 A1 * | 11/2007 | Wang | A61B 18/148 606/41 |
| 2009/0012517 A1 * | 1/2009 | de la Rama | A61B 18/1492 606/41 |
| 2009/0163913 A1 | 6/2009 | Wang et al. | |
| 2010/0030114 A1 | 2/2010 | Nguyen et al. | |
| 2010/0152731 A1 | 6/2010 | de la Rama et al. | |
| 2011/0184406 A1 * | 7/2011 | Selkee | A61B 5/6885 606/41 |
| 2011/0288392 A1 | 11/2011 | de la Rama et al. | |
| 2011/0313417 A1 | 12/2011 | de la Rama et al. | |
| 2012/0265130 A1 * | 10/2012 | de la Rama | A61B 18/1492 604/95.01 |
| 2013/0085479 A1 | 4/2013 | de la Rama et al. | |
| 2014/0330269 A1 | 11/2014 | Pappone et al. | |
| 2014/0343546 A1 | 11/2014 | de la Rama et al. | |

FOREIGN PATENT DOCUMENTS

| | | |
|---|---|---|
| CN | 102166136 A | 8/2011 |
| EP | 1033107 A1 | 6/2000 |
| EP | 2347726 | 7/2011 |

\* cited by examiner

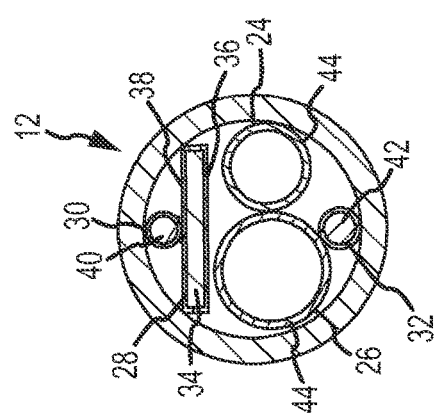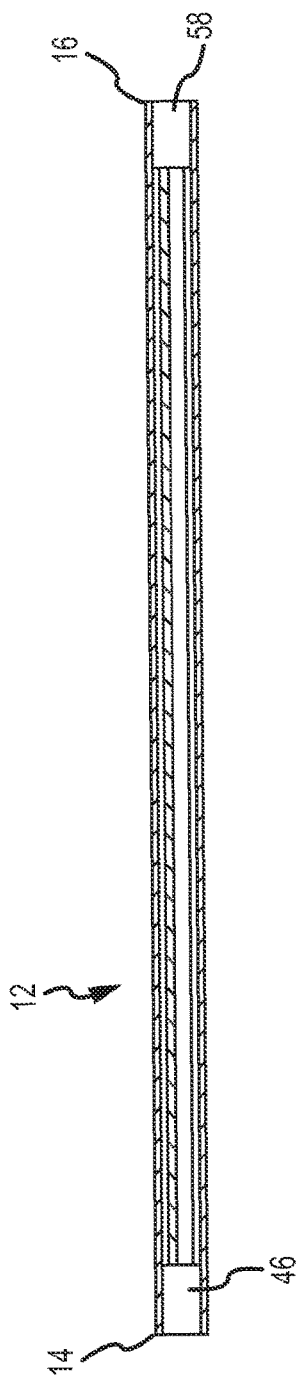
FIG.2B
FIG.3

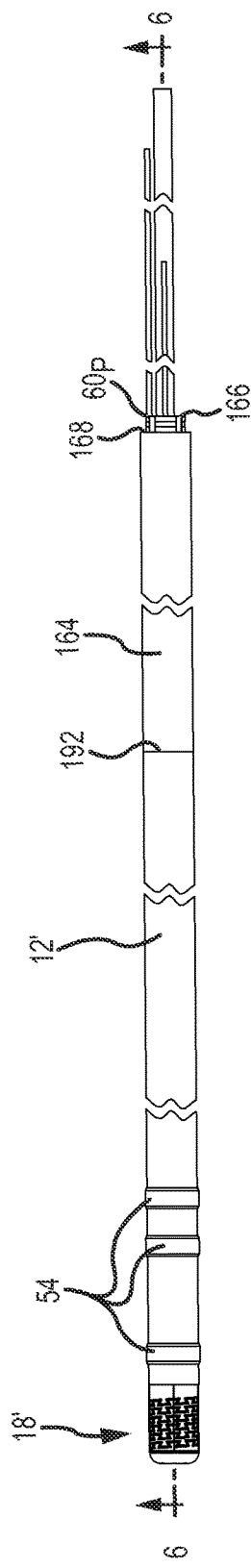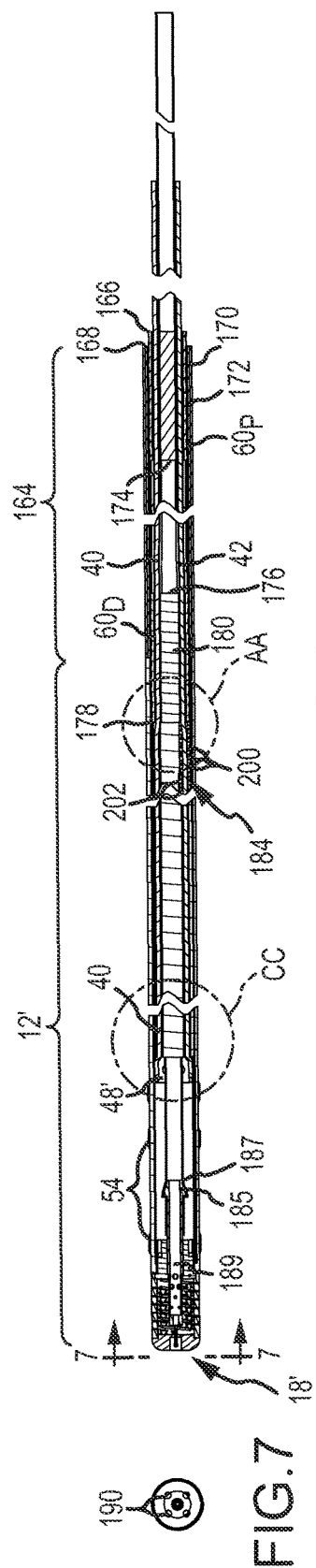
FIG.5
FIG.6
FIG.7

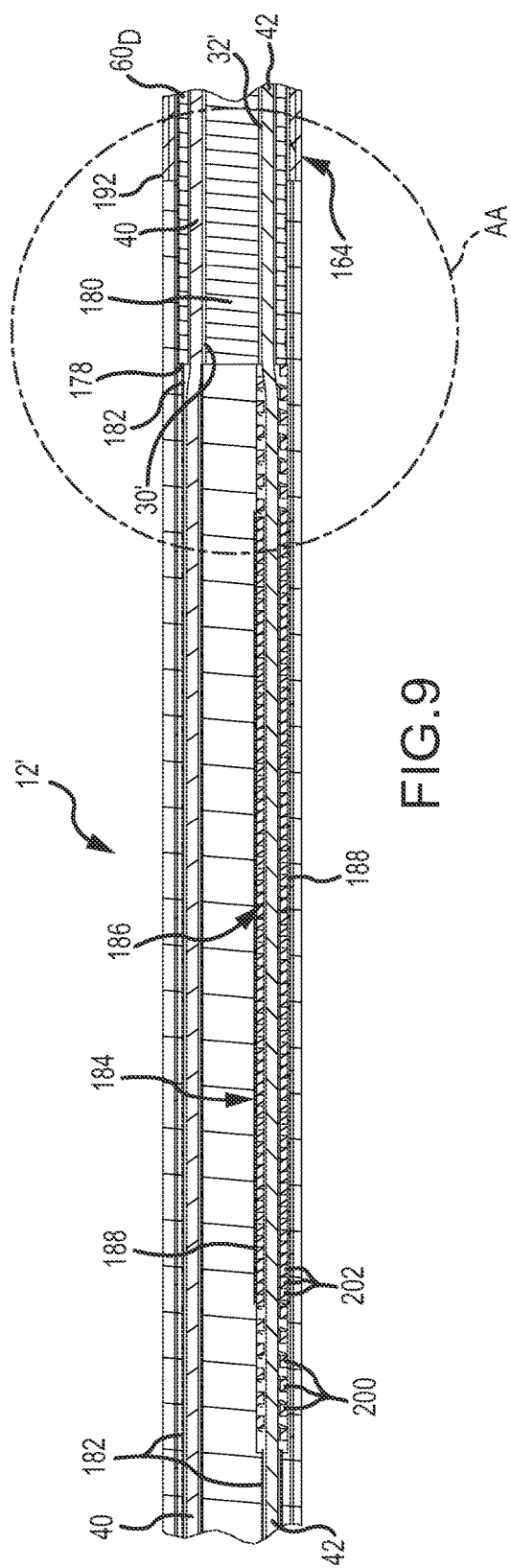
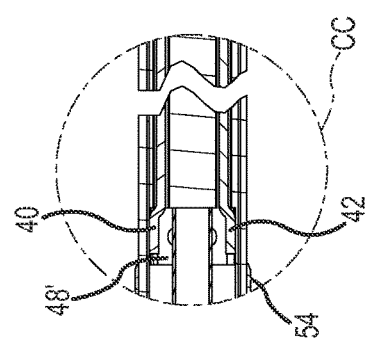

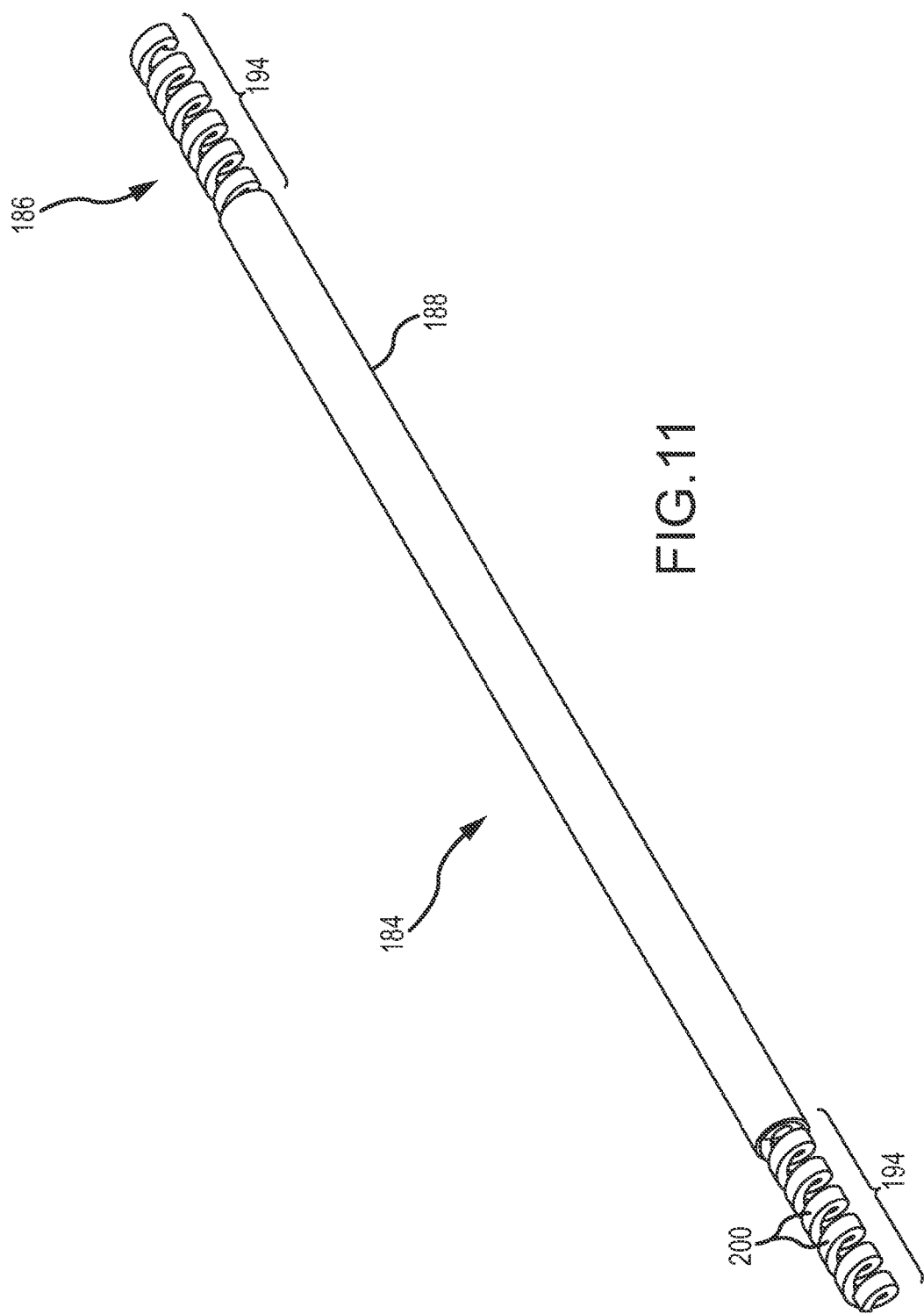

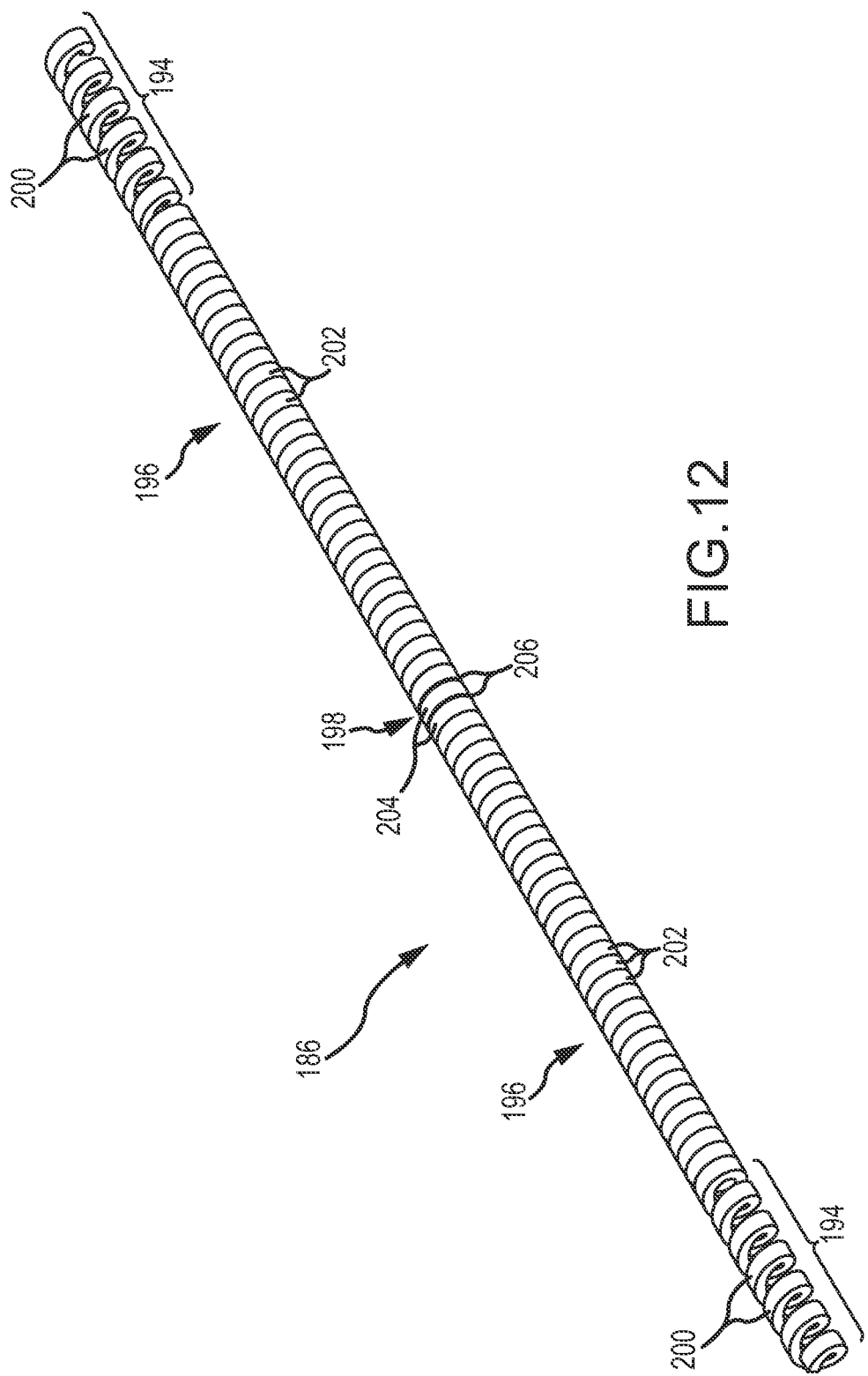

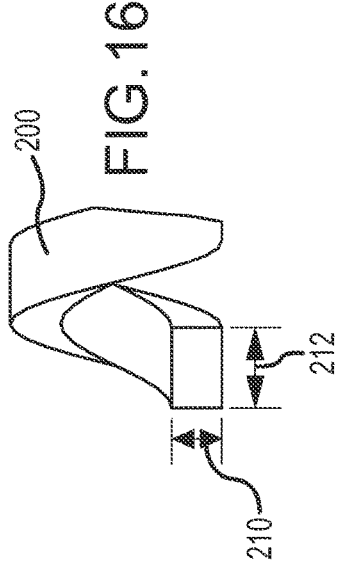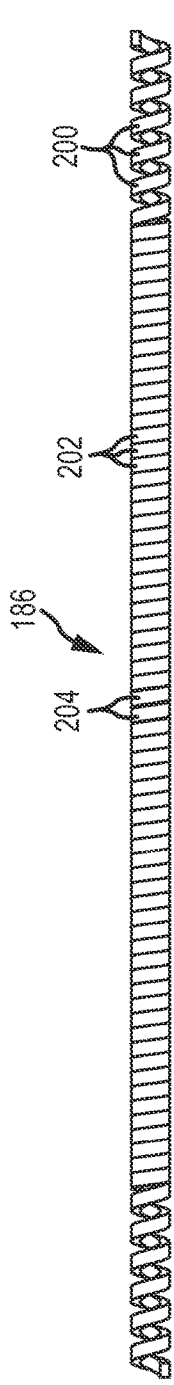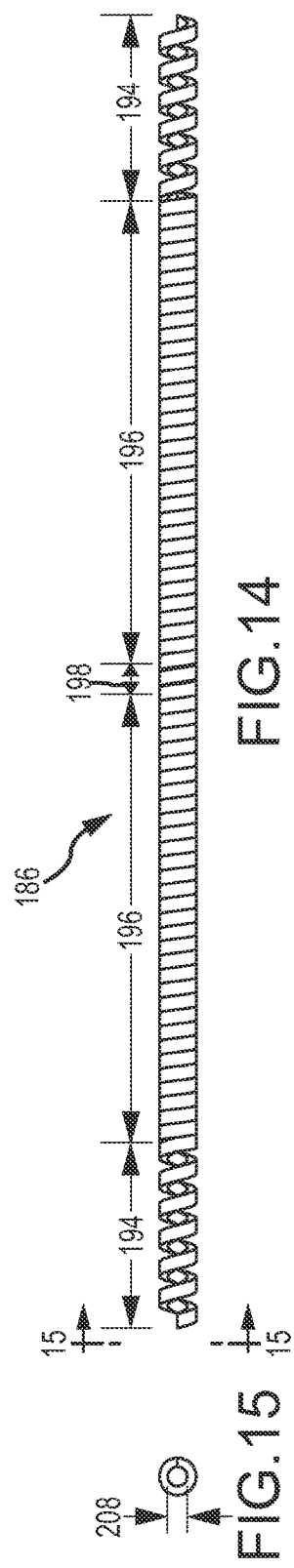

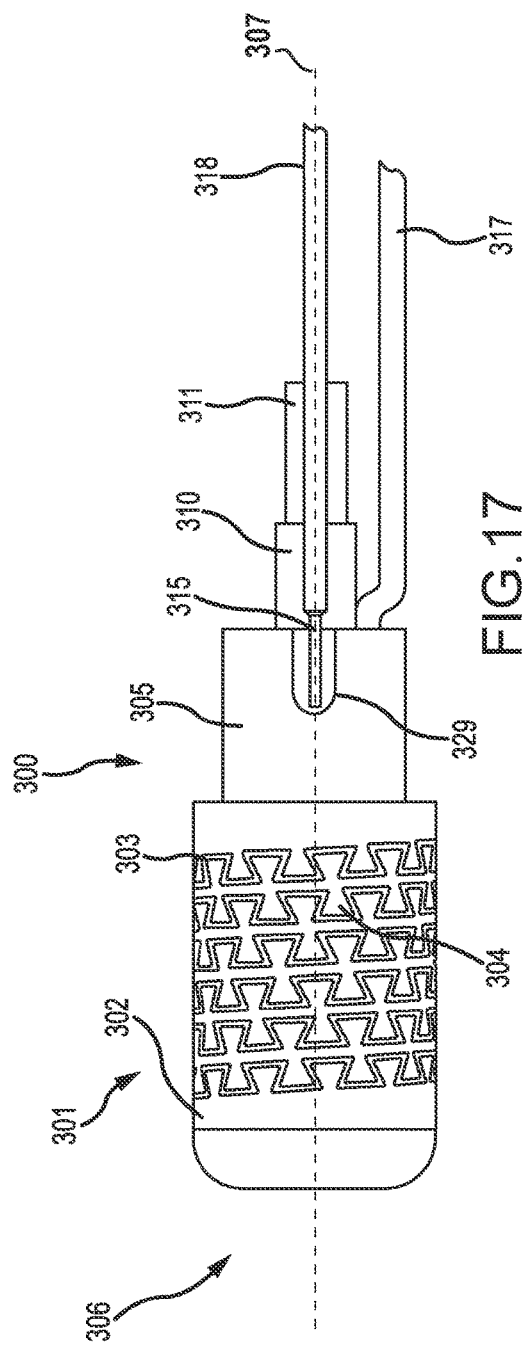
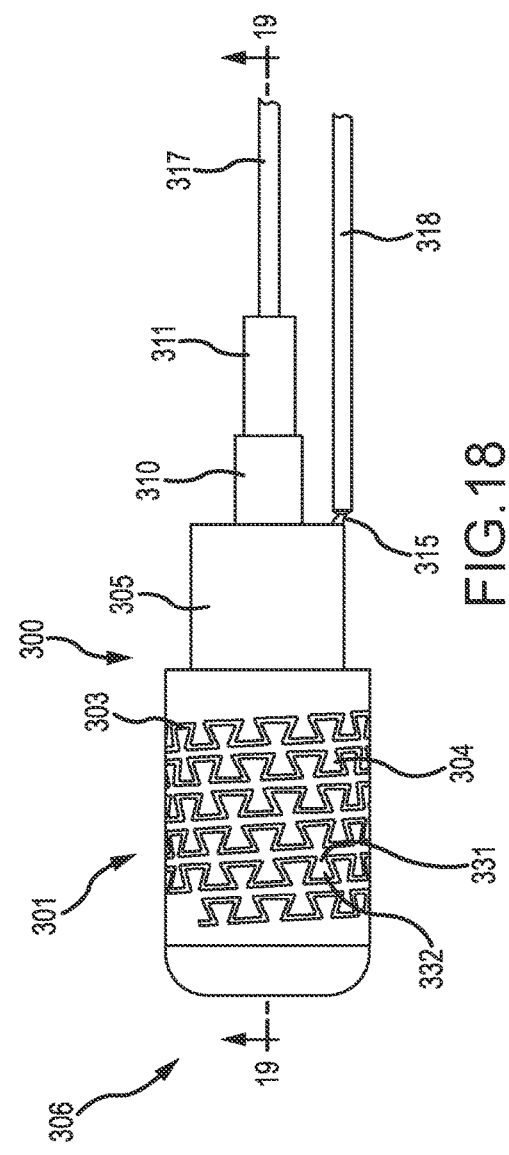
FIG. 17
FIG. 18

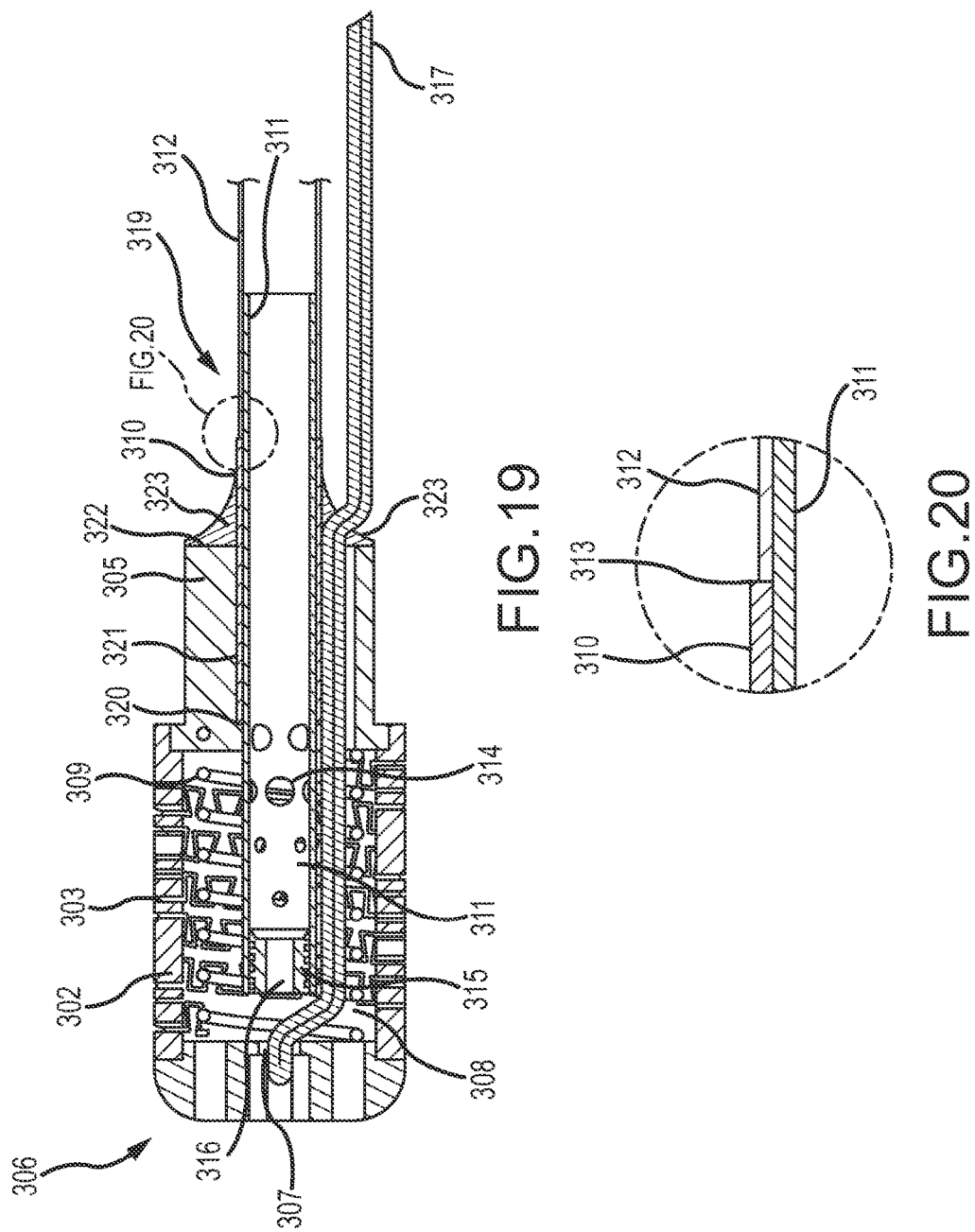

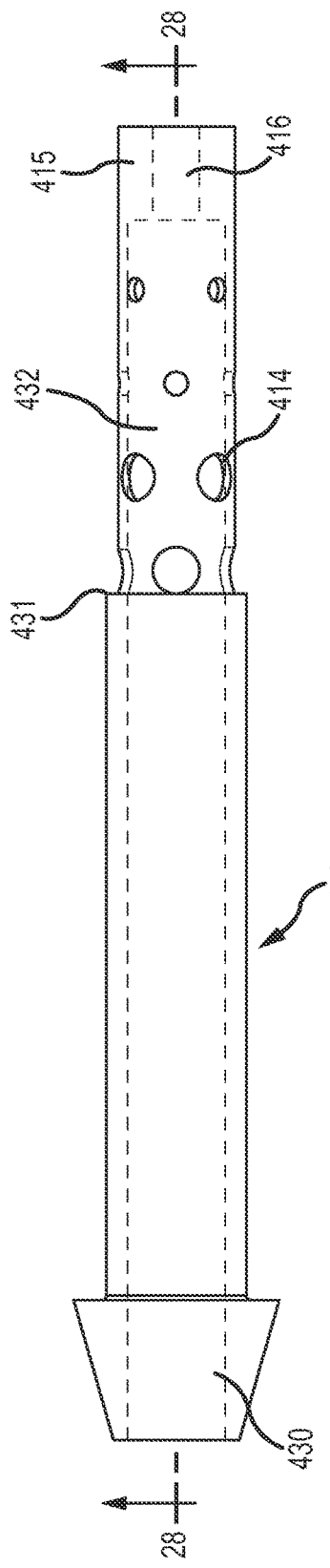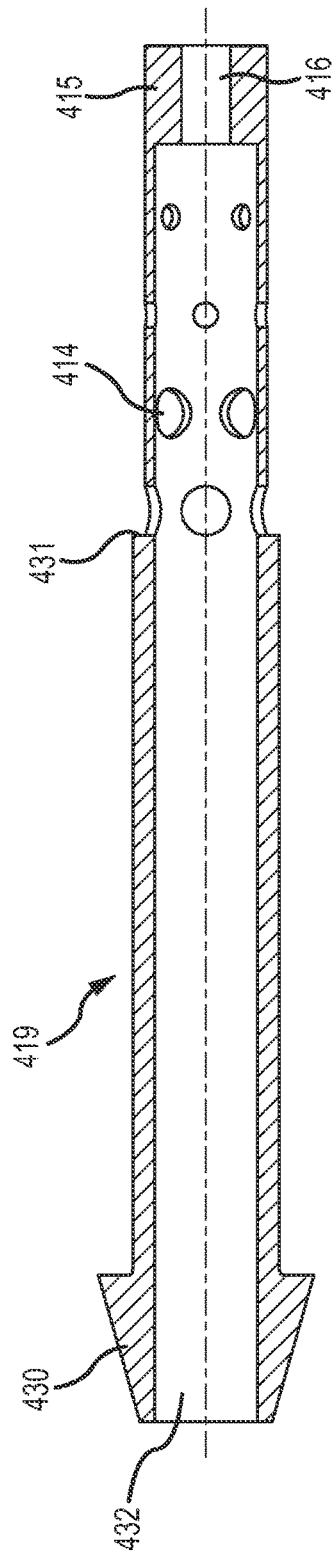

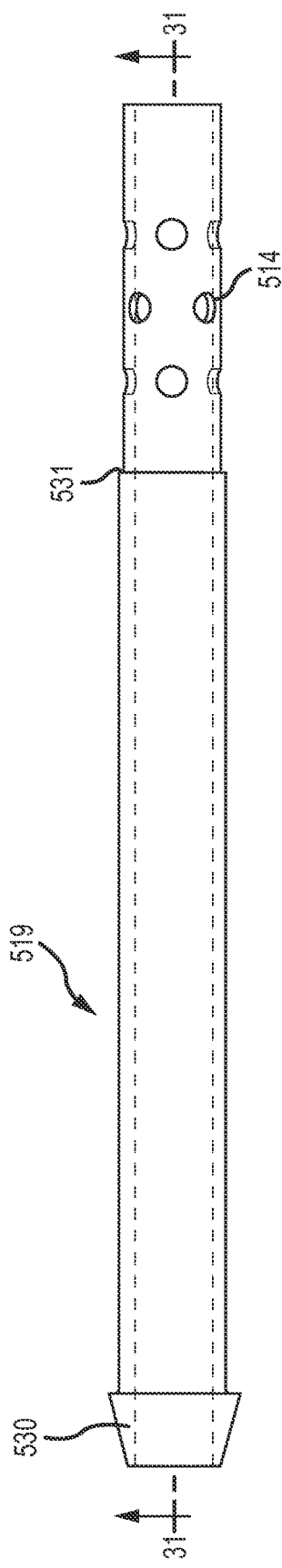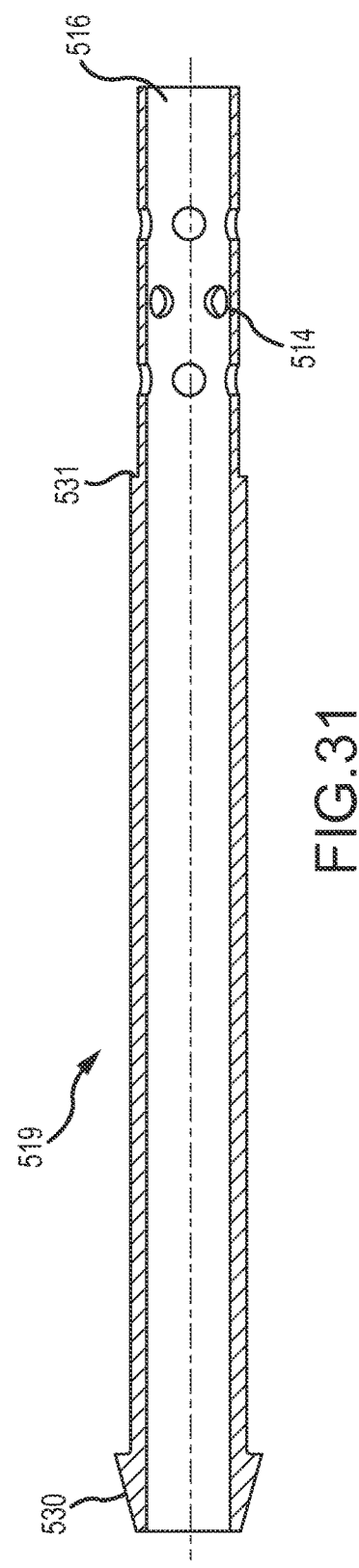

FLEX TIP FLUID LUMEN ASSEMBLY WITH TERMINATION TUBE

CROSS-REFERENCE TO RELATED APPLICATION

This application is a continuation-in-part of U.S. non-provisional patent application Ser. No. 13/838,124, filed 15 Mar. 2013, (the '124 application), which claims the benefit of U.S. provisional patent application No. 61/643,748, filed 7 May 2012 (the '748 application); and this application claims the benefit of provisional patent application No. 61/820,518, filed 7 May 2013 (the 518 application). The '124 application, the '748 application, and the '518 application are all hereby incorporated by reference as though fully set forth herein.

BACKGROUND a. Field

The instant disclosure relates generally to a manifold assembly for delivering irrigant to a catheter tip and irrigated catheter tips incorporating such a manifold assembly.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electro-physiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray errant conduction signals that can form the basis for arrhythmias.

Because RF ablation can generate significant heat, which if not controlled can result in excessive tissue damages, such as steam pop, tissue charring, and the like, it can be desirable to monitor the temperature of ablation electrode assemblies. It can also be desirable to include a mechanism to irrigate the ablation electrode assemblies and/or targeted areas in a patient's body with biocompatible fluids, such as saline solution. The use of irrigated ablation electrode assemblies can also prevent the formation of soft thrombus and/or blood coagulation, as well as enable deeper and/or greater volume lesions as compared to conventional, non-irrigated catheters at identical power settings.

The foregoing discussion is intended only to illustrate the present field and should not be taken as a disavowal of claim scope.

BRIEF SUMMARY

In various embodiments, a catheter tip assembly can comprise a tip electrode comprising a ledge feature, a proximal lumen and a center cavity and a manifold assembly comprising a fluid lumen manifold and a stop tube. The stop tube can be coupled to the fluid lumen manifold and configured to abut the ledge feature such that a distal end of the fluid lumen manifold extends a pre-determined distance into the center cavity of the tip electrode. The catheter tip assembly can further comprise a thermal sensor coupled to the tip electrode. The thermal sensor can be coupled to a distal end of the tip electrode. A distal portion of the fluid lumen manifold can further comprise a plurality of sideholes. The plurality of sideholes can be of varying sizes. In one embodiment a subset of the plurality of sideholes that are more distally located can be a smaller diameter than another subset of the plurality of sideholes that are more proximally located. The catheter tip assembly can further comprise a lumen cap coupled to a distal end of the fluid lumen manifold. The lumen cap can comprise a distal port. The tip electrode of the catheter tip assembly can comprise a flexible tip electrode. The flexible tip electrode can comprise an electrode wall, a coil, a linear gap, and a proximal stem. The linear gap can extend through the electrode wall and can be configured to allow an irrigant therethrough.

In various embodiments, a catheter can comprise a tip electrode comprising a ledge feature, a proximal lumen and a center cavity and a manifold assembly can comprise a barbed connector, a stop shoulder, and a plurality of sideholes. The manifold assembly can be configured to abut the ledge feature such that a distal end of the manifold assembly extends a pre-determined distance into the center cavity of the tip electrode. The manifold assembly can further comprise a sensor depression. The sensor depression can be sized and configured to couple to a location sensor. The catheter can further comprise a catheter body coupled to the tip electrode. The catheter can further comprise a deflectable catheter shaft section coupled to the tip electrode. The deflectable catheter shaft section can comprise an elongated body extending along a longitudinal axis and can comprise a distal end and a proximal end and a plurality of lumens extending along the longitudinal axis of the elongated body. At least one of the plurality of lumens can abut at least another one of the plurality of lumens. The manifold assembly can comprise PEEK.

In various embodiments, a flexible tip electrode can comprise an electrode wall, a linear gap, a proximal stem, a ledge feature, and a proximal face and a manifold assembly comprising a fluid lumen manifold and a stop tube. The manifold assembly can be configured to engage with the ledge feature such that a proximal end of the stop tube is a predetermined distance from the proximal face of the flexible tip electrode. The flexible tip electrode can further comprise a tapered fluid lumen that can be configured to couple to the fluid lumen manifold and abut the stop tube.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 2B is a cross-sectional view of the deflectable catheter shaft section of FIG. 1 taken along line 2B-2B seen in FIG. 2A.

FIG. 3 is a longitudinal, side cross-sectional view of the deflectable catheter shaft section of FIG. 1 taken along line 3-3, with various components of the catheter omitted for the purposes of clarity.

FIG. 5 is a fragmentary view of a deflectable catheter shaft section and an intermediate catheter shaft section.

FIG. 6 is a cross-sectional view taken along line 6-6 of FIG. 5.

FIG. 7 is an end view taken in the direction of line 7-7 of FIG. 6.

FIG. 8 is an enlarged view of circled region CC shown in FIG. 6.

FIG. 9 is an enlarged, fragmentary, cross-sectional view of a portion of the deflectable catheter shaft section depicted in FIGS. 5 and 6, and includes an enlarged view of the region within dashed circle AA of FIG. 6.

FIG. 11 is an isometric view of a bendable stiffening member, which include in this embodiment a coil support tube and a multi-pitch coil.

FIG. 12 is an isometric view of a multi-pitch coil.

FIGS. 13 and 14 depict two additional views of the multi-pitch coil depicted in FIG. 12.

FIG. 15 is an end view of the multi-pitch coil taken along line 15-15 of FIG. 14.

FIG. 16 is an enlarged, fragmentary view of a portion of the coil depicted in FIGS. 12-15.

FIG. 17 is a fragmentary view of a flexible tip assembly in accordance with an embodiment.

FIG. 18 is a fragmentary view of the flexible tip assembly depicted in FIG. 17 rotated 90 degrees about a longitudinal axis of the flexible tip assembly.

FIG. 19 is a cross-sectional view of the flexible tip assembly of FIGS. 17 and 18 taken along line 19-19.

FIG. 20 is an enlarged view of the circled region labeled "FIG. 20" of FIG. 19.

FIG. 27 is a side view of a manifold assembly in accordance with an embodiment.

FIG. 28 is a cross-sectional view of the manifold assembly depicted in FIG. 27 taken along line 28-28.

FIG. 30 is a side view of a manifold assembly in accordance with an embodiment.

FIG. 31 is a cross-sectional view of the manifold assembly depicted in FIG. 30 taken along line 31-31.

DETAILED DESCRIPTION OF THE DISCLOSURE

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
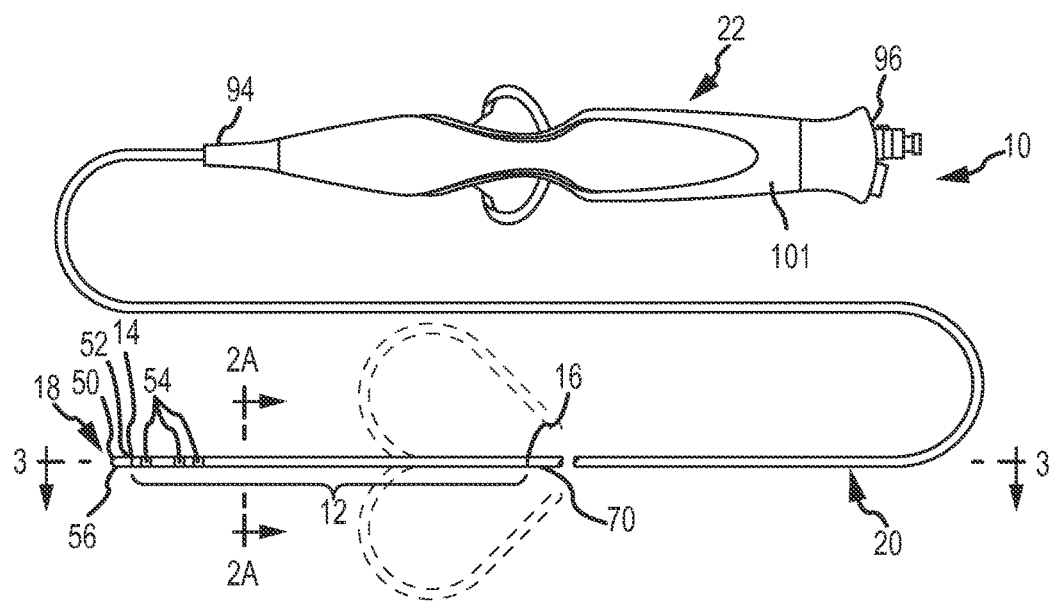
FIG. 1 is a schematic view of a catheter incorporating a deflectable catheter shaft section in accordance with an embodiment.

FIG. 1 generally illustrates a deflectable electrophysiology catheter 10 that comprises a deflectable catheter shaft section 12 in accordance with an embodiment. Deflectable catheter shaft section 12 comprises an elongated body having a distal end 14 and a proximal end 16. In its most general form, catheter 10 further comprises a tip assembly 18 located at the distal end 14 of the deflectable catheter shaft section 12, a proximal catheter shaft section 20 located at the proximal end 16 of the deflectable catheter shaft section 12, and a handle assembly 22. Catheter 10 may be used in any number of diagnostic and therapeutic applications, such as the recording of electrograms in the heart, the performance of a cardiac ablation procedure, and other similar applications/procedures. Accordingly, one of ordinary skill in the art will recognize and appreciate that the inventive deflectable catheter shaft section and method of manufacturing the same can be used in any number of diagnostic and therapeutic applications.

Still referring to FIG. 1, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of the proximal catheter shaft section 20.

Figure 2A:
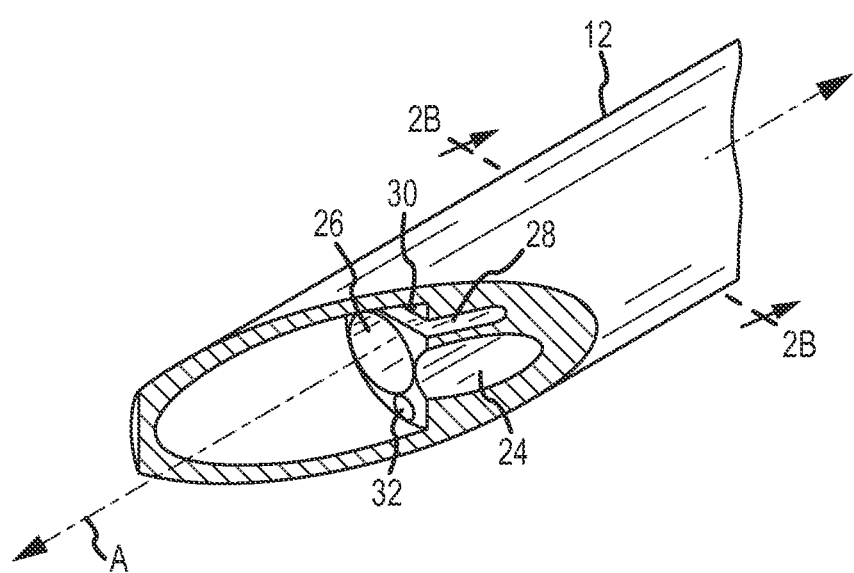
FIG. 2A is a partially cut-away isometric view of the deflectable catheter shaft section of FIG. 1 taken along line 2A-2A, with various components of the catheter omitted for the purposes of clarity.

Referring now to FIG. 2A, deflectable catheter shaft section 12 extends along a longitudinal axis A and comprises at least five substantially separate lumens 24, 26, 28, 30, 32, each extending along the longitudinal axis A from the distal end 14 to the proximal end 16 in accordance with an embodiment. Each of the plurality of lumens 24, 26, 28, 30, 32 can be fully formed in accordance with an embodiment. In particular, each of the plurality of lumens can be a desired shape as described hereinbelow. Depending upon the intended application of the catheter 10, each lumen 24, 26, 28, 30, 32 may extend along an entire length of the deflectable catheter shaft section 12 or may extend less than the entire length of the deflectable catheter shaft section 12. Each lumen 24, 26, 28, 30, 32 may be formed to have a predetermined cross-sectional profile and shape. Each lumen 24, 26, 28, 30, 32 is configured such that various components required for performing the particular functionality of the catheter 10 (e.g., recording electrograms, ablation, ultrasound, etc.) are disposed therein.

Referring now to FIGS. 2A and 2B, first lumen 24 may be generally round in cross-sectional shape. Although this particular shape is mentioned in detail, the cross-sectional shape of the first lumen 24 may vary in accordance with various embodiments. First lumen 24 may be configured for housing wiring for electrodes as described in more detail hereinbelow or for other electrical components.

Second lumen 26 may be located generally adjacent to or abutting the first lumen 24 within deflectable catheter shaft section 12. In accordance with an embodiment, the first and second lumens 24, 26 may be disposed as proximate each other as manufacturally feasible, while allowing the first and second lumens 24, 26 to be fully formed. For example and without limitation, the distance between first lumen 24 and second lumen 26 may be less than about 0.015 inches (0.38 mm) in accordance with an embodiment. In an embodiment, the first lumen 24 and the second lumen 26 may be connected to each other. Second lumen 26 may be generally round in cross-sectional shape. Although this particular shape is mentioned in detail, the cross-sectional shape of the second lumen 26 may vary in accordance with various embodiments. Second lumen 26 may be configured for use as an irrigation fluid passageway and the like.

Third lumen 28 may be located generally adjacent to or abutting both first and second lumens 24, 26. In accordance with an embodiment, the third lumen 28 and the first and second lumens 24, 26 may be disposed as proximate each other as manufacturally feasible, while allowing the first, second, and third lumens 24, 26, 28 to be fully formed. For example and without limitation, the distance between third lumen 28 and at least one of the first lumen 24 and second lumen 26 may be less than about 0.015 inches (0.38 mm) in accordance with an embodiment. In an embodiment, the third lumen 28 and at least one of the first lumen 24 and the second lumen 26 may be connected to each other. Third lumen 28 may be generally rectangular in cross-sectional shape. Although this particular shape is mentioned in detail, the cross-sectional shape of the third lumen 28 may vary in accordance with various embodiments. Third lumen 28 may be configured to house a planarity wire 34 (FIG. 2B). The planarity wire 34 has opposing flat surfaces 36, 38 and is configured to maintain the planarity of the deflectable catheter shaft section 12 as the deflectable catheter shaft section 12 deflects.

Fourth and fifth lumens 30, 32 may be located on opposing sides of the third lumen 28 for the planarity wire 34. The fourth lumen 30 may be located generally adjacent to or abutting the third lumen 28. In accordance with an embodiment, the third and fourth lumen 28, 30 may be disposed as proximate each other as manufacturally feasible, while allowing the third and fourth lumens 28, 30 to be fully formed. For example and without limitation, the distance between fourth lumen 30 and the third lumen 28 may be less than about 0.010 inches (0.254 mm). In an embodiment, the fourth lumen 30 and the third lumen 28 may be connected to each other. The fifth lumen 32 may be located generally adjacent to or abutting the second lumen 26. In accordance with an embodiment, the second and fifth lumens 26, 32 may be disposed as proximate each other as manufacturally feasible, while allowing the second and fifth lumens 26, 32 to be fully formed. For example and without limitation, the distance between the fifth lumen 32 and the second lumen 26 may be less than about 0.010 inches (0.254 mm). In an embodiment, the fifth lumen 32 and the second lumen 26 may be connected to each other. The fourth and fifth lumens 30, 32 may be generally round in cross-sectional shape. Although these particular shapes are mentioned in detail, the cross-sectional shape of the fourth and fifth lumens 30, 32 may vary in accordance with various embodiments.

Fourth and fifth lumens 30, 32 may be configured to each house a pull wire 40, 42 (FIG. 2B) to enable the deflectable catheter shaft section 12 to deflect in two or more directions. In particular, the handle assembly 22 described in more detail hereinbelow may comprise at least one pull wire 40, 42 operatively connected to it to facilitate deflection of the deflectable catheter shaft section 12. Although the deflectable catheter shaft section 12 is described and illustrated as including two opposing pull wires 40, 42, it should be noted that the deflectable catheter shaft section 12 of catheter 10 is not limited to two opposing pull wires 40, 42. Rather, the deflectable catheter shaft section 12 of catheter 10 may include a single pull wire arrangement in other embodiments. The deflectable catheter shaft section 12 of catheter 10 may include more than two pull wires in other embodiments. The pull wires 40, 42 may be formed from a superelastic nickel-titanium (known as NiTi or Nitinol) wire, carbon fiber, para-aramid synthetic fiber generally available from DuPont under the brand name KEVLAR®, or other suitable material in accordance with various embodiments.

Still referring to FIG. 2B, each of the lumens 24, 26, 28, 30, 32 may be lined with liners 44 that serve the purpose of providing a lubricious surface (e.g., to allow for the sliding of the pull wires) and insulating the components within the lumens 24, 26, 28, 30, 32. If provided, the liners 44 may be constructed of a polymeric material, such as PTFE or any other suitable material.

Figure 4A:
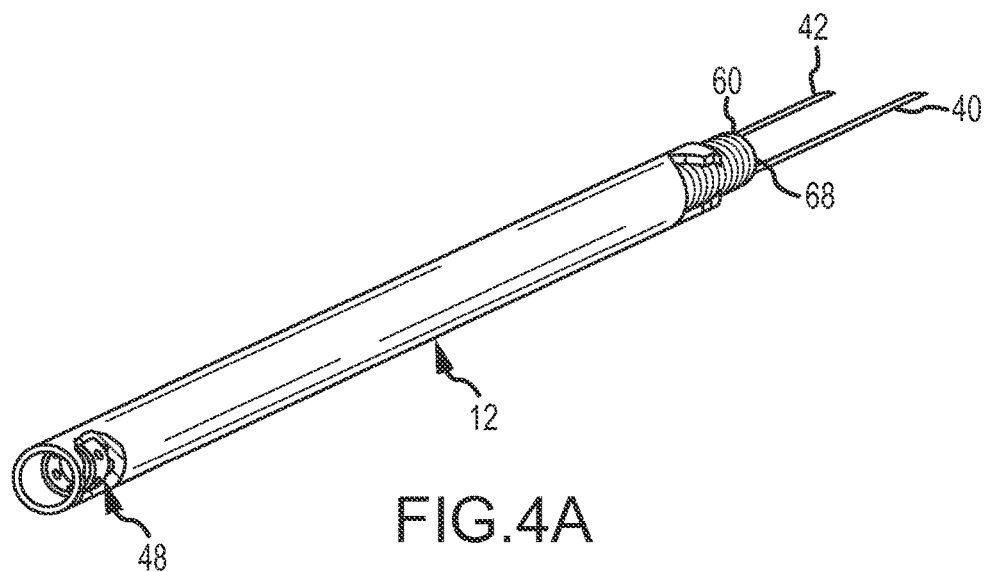
FIG. 4A is a partially cut-away, isometric view of the deflectable catheter shaft section of FIG. 1, showing a shaft coupler in accordance with an embodiment.

Referring now to FIG. 3, deflectable catheter shaft section 12 comprises a first pocket 46 at distal end 14 configured to accept a pull ring 48 (FIG. 4A). Pull wires 40, 42 are attached to diametrically opposite locations on the pull ring 48 by a solder or weld joint, for example and without limitation. The pull wires 40, 42 then extend from the pull ring 48 toward the handle assembly 22. Pulling of the pull wires 40, 42 by the handle assembly 22 during use of the catheter 10 will cause the pull ring 48 to tilt or rock, thereby deflecting the deflectable catheter shaft section 12. The first pocket 46 at distal end 14 is also configured to accept tip assembly 18.

Referring back to FIG. 1, tip assembly 18 comprises a tip electrode 56 having a distal end 50 and a proximal end 52. Tip electrode 56 may be configured for various functions and may include, without limitation, an active outer surface that is configured for exposure to blood and/or tissue. The tip electrode 56 may be affixed to distal end 14 of the deflectable catheter shaft section 12 in a number of ways. For instance, the tip electrode 56 may be bonded to an inner radial surface of the deflectable catheter shaft section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 56 of the tip assembly 18 may have a recess (not shown) formed therein that is sufficiently sized and configured to receive a wire (not shown) that is connected to the tip electrode 56. One end of the wire is connected to the tip electrode 56 and the other end is connected to, for example, monitoring or recording or ablation devices, such as a radiofrequency (RF) generator. The wire is typically a pre-coated wire that is insulated from other components in the tip assembly 18. The tip electrode 56 of the tip assembly 18 may further include a recess (not shown) formed therein that is configured to receive a thermocouple (not shown). The thermocouple may be configured to measure the temperature of the tip electrode 56, targeted tissue, and/or the interface therebetween and provide feedback to the monitoring or recording or ablation devices described hereinabove. The tip electrode 56 may further include a fluid lumen configured as a passageway for irrigation fluid.

Figure 4B:
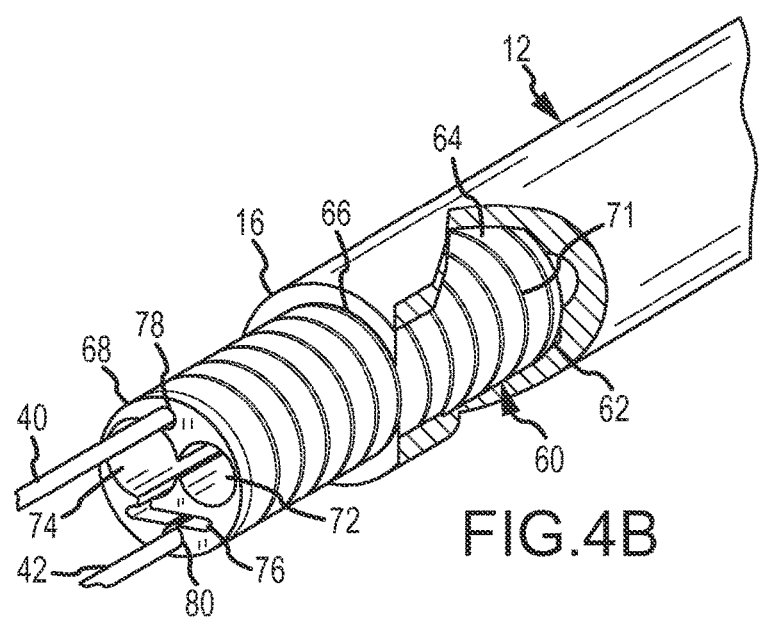
FIG. 4B is a partially cut-away, isometric view of the deflectable catheter shaft section of FIG. 1 showing a shaft coupler in accordance with an embodiment.

Referring back to FIG. 3, deflectable catheter shaft section 12 comprises a second pocket 58 at proximal end 16 configured to accept a shaft coupler 60 (FIGS. 4A-4B). Referring to FIGS. 4A-4B, the shaft coupler 60 is configured to connect the deflectable catheter shaft section 12 to the proximal catheter shaft section 20. A distal end 62 of the shaft coupler 60 can be affixed to the proximal end 16 of the deflectable catheter shaft section 12 in a number of ways. For instance, an outer radial surface 64 of the shaft coupler 60 may be bonded to an inner radial surface 66 of the deflectable catheter shaft section 12 using an epoxy material, for example and without limitation. A proximal end 68 of the shaft coupler 60 can be affixed to a distal end 70 (FIG. 1) of the proximal catheter shaft section 20 in a number of ways. For instance, the outer radial surface 64 of the shaft coupler 60 may be bonded to an inner radial surface (not shown) of the proximal catheter shaft section 20 using an epoxy material, for example and without limitation. The outer radial surface 64 of the shaft coupler 60 can comprise a helical groove 71 in accordance with some embodiments. The helical groove 71 can be configured to have a variable depth in accordance with various embodiments. The helical groove 71 can be configured to improve bonding between the shaft coupler 60 and the deflectable catheter shaft section 12 in accordance with various embodiments. For example, in at least one embodiment the groove 71 may be configured to hold an adhesive added during manufacturing of the catheter 10. In another embodiment, the groove 71 may be configured to bond and/or grab onto various portions of the shaft sections 12 and 20 during a reflow process, described in more detail below. In another embodiment, the helical groove 71 may be configured both to hold an adhesive and bond/grab onto the shaft sections 12 and 20 during a reflow process. The shaft coupler 60 can be generally cylindrical in shape. The shaft coupler 60 can also include a plurality of lumens 72, 74, 76, 78, 80 in communication with lumens 24, 26, 28, 30, 32 of deflectable catheter shaft section 12, which function as an electrical lumen, fluid lumen, planarity wire lumen, and pull wire lumens, respectively.

Referring again to FIG. 1, proximal catheter shaft section 20 can also include one or more lumens (not shown). Generally, proximal catheter shaft section 20 can include a single lumen. The single lumen can be in communication with lumens 72, 74, 76, 78, 80 of shaft coupler 60, which are in turn in communication with lumens 24, 26, 28, 30, 32 of deflectable catheter shaft section 12. Proximal catheter shaft section 20 can also be constructed of a series of polymer layer(s) and braid structure(s). In particular, one or more wires wound to form a cylindrical braid structure can substantially surround the one or more lumens of proximal catheter shaft section 20. In addition, a polymeric material, such as polyurethane, nylon, or various types of plastic materials such as polyether block amides offered under the trademark PEBAX®, or any other suitable material, can also substantially surround the one or more lumens of proximal catheter shaft section 20. Regardless of the material used, the material must have capability to be displaced or to shrink when subjected to a process, such as for example, a heating process that is performed. The mechanical properties of the proximal catheter shaft section 20 can also be varied by varying the properties of the cylindrical braid structure(s) and the polymeric material (e.g., dimension of the cylindrical braid structure and/or durometers of the polymers). Additionally, the mechanical properties of the proximal catheter shaft section 20 can be varied along the length of the proximal catheter shaft section 20 in accordance with some embodiments of the disclosure or can be substantially constant along the entire length of the proximal catheter shaft section 20 in accordance with other embodiments of the disclosure.

The handle assembly 22 is coupled to the proximal catheter shaft section 20 at its proximal end (disposed within handle assembly 22 and not shown). The handle assembly 22 is operative to, among other things, effect movement (i.e., deflection) of the deflectable catheter shaft section 12. The handle assembly 22 includes a distal end 94 and a proximal end 96. Referring now to FIGS. 9A and 9B and as will be described in greater detail below, the handle assembly 22 includes an actuator 98 that can be selectively manipulated to cause deflectable catheter shaft section 12 to deflect in one or more directions (e.g., up, down, left, and right). Deflectable catheter shaft section 12 may be configured for uni-directional deflection in accordance with some embodiments and may be configured for bi-directional deflection in accordance with other embodiments.

The catheter 10 may include any number of other elements such as, for example and without limitation, thermocouples, thermistor temperature sensors, etc. for monitoring the temperature of targeted tissue and controlling the temperature.

FIGS. 5 and 6 depict a deflectable catheter shaft section 12' similar to the deflectable catheter shaft section 12 shown to good advantage in, for example, FIGS. 1, 3, and 4A. As shown in FIGS. 5 and 6, the catheter shaft may include the deflectable catheter shaft section 12', an intermediate catheter shaft section 164, and a proximal catheter shaft section (not shown in FIGS. 5 and 6, but the proximal catheter shaft section, if present, would abut the right longitudinal end, as oriented in FIGS. 5 and 6, of the intermediate catheter shaft section 164). In this embodiment, two shaft couplers are used, including a proximal shaft coupler $60_P$ for coupling the proximal catheter shaft section to the intermediate catheter shaft section 164, and a distal shaft coupler $60_D$ for coupling the intermediate catheter shaft section 164 to the deflectable catheter shaft section 12'.

In at least one embodiment, the proximal catheter shaft section may comprise a portion of the handle assembly, e.g., the proximal catheter shaft section may comprise a pocket (not shown) sized and configured to receive a proximal shaft coupler $60_P$ and formed in the distal end 94 of handle assembly 22 seen in FIG. 1. In an alternative embodiment, it is possible, depending upon which handle assembly 22 is selected, that the handle assembly may connect to the proximal end 168 of the intermediate catheter section 164, or to the proximal end 166 of the proximal shaft coupler $60_P$. In these latter configurations, the intermediate catheter shaft section 164 would be analogous to the proximal catheter section shown in, for example, FIG. 1.

Referring more particularly to FIG. 6, additional details will be described. FIG. 6 is a cross-sectional view taken along line 6-6 of FIG. 5. Starting from the right side of FIG. 6 and moving leftward, a proximal end 166 of the proximal shaft coupler $60_P$ may be seen extending proximally beyond the proximal end 168 of the intermediate catheter shaft section. It is also possible to see that the intermediate catheter shaft section 164 may include a first shaft material 170 (e.g., PEBAX) and a second shaft material 172 (e.g., PEBAX or braided mesh). A first pull wire 40 may be seen extending along the upper portion of the proximal shaft coupler $60_P$, and a second pull 42 wire may be seen extending adjacent a lower portion of the proximal shaft coupler $60_P$. The portion of these pull wires 40, 42 extending from the proximal end 166 of the proximal shaft coupler $60_P$ back to the handle assembly 22 (see, for example, FIG. 1) may have compression coils surrounding them. Additionally, there may be compression coils (not shown) extending between a distal end 174 of the proximal shaft coupler $60_P$ and a proximal end 176 of the distal shaft coupler $60_D$. These compression coils would be under compression (e.g., they may be compressed 0.070 in.) to help mitigate against undesirable deformation of the intermediate catheter shaft section 164 extending between the proximal and distal shaft couplers. In the embodiment shown, the compression coils do not extend through the proximal shaft coupler, but they could in an alternative embodiment.

Moving further leftward in FIG. 6, you next encounter the distal shaft coupler $60_D$, which is depicted as joining the intermediate catheter shaft section 164 (which, as discussed above, may extend to the handle assembly 22) to the deflectable catheter shaft section 12' that extends from the distal shaft coupler to the tip assembly 18'. A distal end 178 of the distal shaft coupler $60_D$ may be seen to better advantage in FIG. 9, which is an enlarged view of the portion of the catheter within dashed circle AA of FIG. 6. Since both FIGS. 6 and 9 are longitudinally-extending, cross-sectional views, it is possible to see a vertical web 180 (i.e., a line of shaft coupler material) located between the larger lumen 24',26' and extending vertically between the first pull wire lumen 30', and the second pull wire lumen 32'. You may also see a portion of the same coupler material above the first pull wire lumen 30' and below the second pull wire lumen 32'. As shown in FIGS. 6 and 9, when the first pull wire 40 exits the distal end 178 of the distal shaft coupler $60_D$, it enters a liner 182 (e.g., a thin-walled PTFE tube). The second pull wire 42, upon exiting the distal end 178 of the distal shaft coupler $60_D$, extends through a bendable stiffening member (e.g., a 'coil pack' or a 'spring pack' or an 'uncompacted spring pack' or a 'deflection facilitator') 184, the proximal end of which is visible in FIG. 6. The construction of the bendable stiffening member 184 in the deflectable catheter shaft section 12' will be described in more detail below with reference to, for example, FIGS. 9 and 11-16.

As shown to good advantage in dashed circle CC depicted in both FIGS. 6 and 8, the first and second pull wires 40, 42 are attached to diametrically opposed locations on the pull ring 48'. Distal to the pull ring 48' in the configuration depicted in FIGS. 5 and 6 are a plurality of ring electrodes 54 followed distally by a tip assembly 18', including, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2 and United States patent application publication no. US 2010/0152731 A1, each of which is hereby incorporated by reference as though fully set forth herein. The tip assembly 18', as depicted in FIG. 6, also includes a barbed connector 185 that locks into a complementary pocket 187, thereby facilitating delivery of irrigant to a ported fluid distribution tube 189. FIG. 7 is an end view of the tip assembly 18' (looking in the direction of the arrows on line 7-7 of FIG. 6) and illustrates a plurality of irrigation ports 190 through the distal surface of the tip.

As may be seen in FIGS. 9 and 11, the bendable stiffening member 184 includes, in this embodiment, a multi-pitch coil 186 (see FIG. 12 for an isometric view of the multi-pitch coil) that is partially covered by a coil support tube 188. This coil support tube may be, for example, a polyimide tube or a NiTi tube or a tube constructed from some other flexible material capable of bending with and supporting the internal coil 186 comprising part of the bendable stiffening member. As also shown to good advantage in FIG. 9, when the second pull wire 42 exits the distal end of the bendable stiffening member 184, it enters a liner 182 (e.g., a thin-walled PTFE tube). The first and second pull wires 40, 42 then continue distally to a pull ring 48'.

Figure 10:
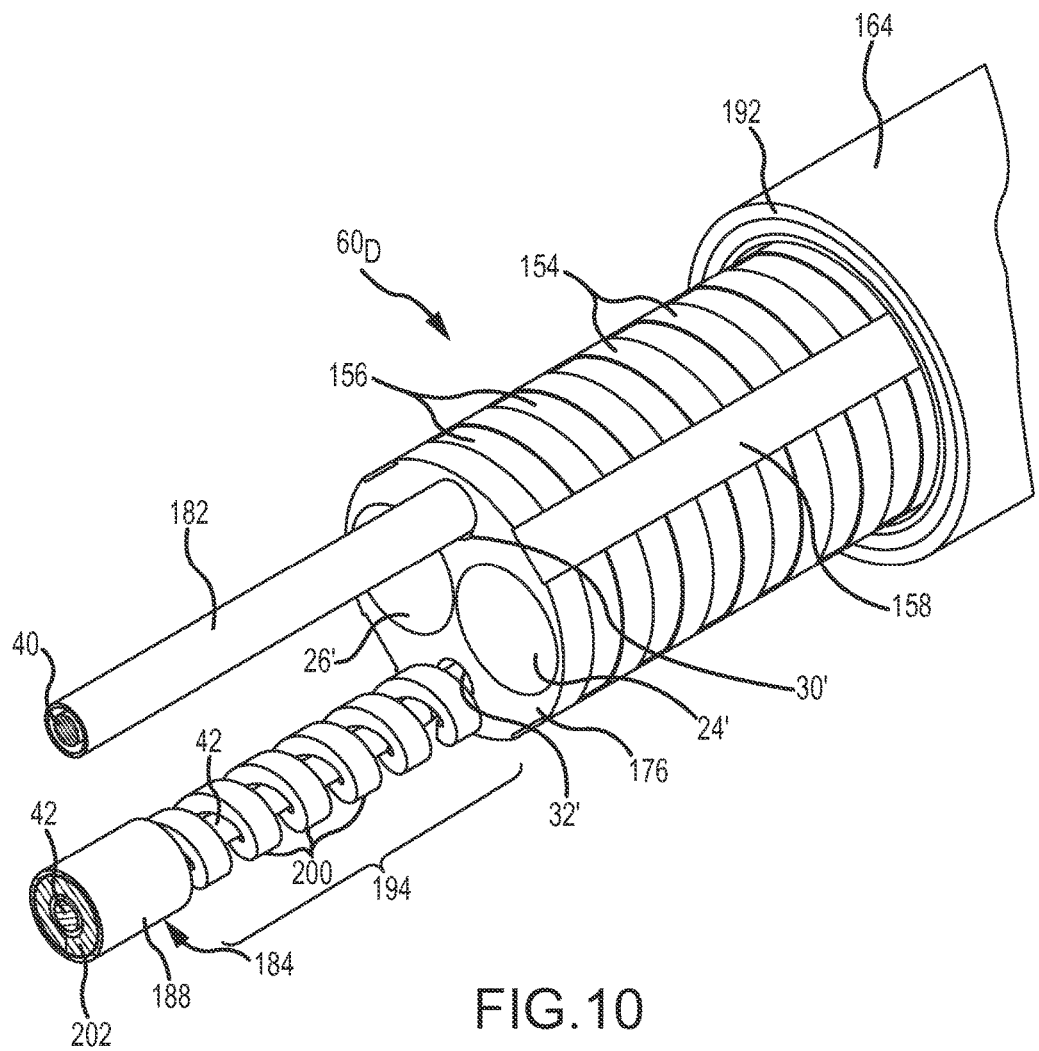
FIG. 10 is a fragmentary, isometric view of a distal shaft coupler mounted in the longitudinal end of an intermediate catheter shaft section, and depicts short sections of the first and second pull wires extending from the distal end of the distal shaft coupler.

FIG. 10 is an enlarged, fragmentary, isometric view of the distal end 176 of the distal shaft coupler 60$_D$. In the figure, the outer shaft material has been removed for clarity. As shown in FIG. 10, the proximal portion of the distal shaft coupler 60$_D$ is mounted in the intermediate catheter shaft section 164 and is shown extending from the distal end 192 of the intermediate catheter shaft section 164. The first pull wire lumen 30' has a first pull wire 40 extending from it, and that first pull wire is covered by a liner 182. The second pull wire 42 is shown extending distally from the second pull wire lumen 32'. The second pull wire is depicted surrounded by a bendable stiffening member, such as the bendable stiffening member 184 depicted in FIG. 11. In FIG. 10, however, only the proximal portion of the bendable stiffening member 184 is shown. In particular, in FIG. 10, a proximal, spaced-coil portion 194 of a multi-pitch coil 186 is shown, as is a proximal portion of the coil support tube 188. Additionally, a portion of one coil 202 of a stacked-coil portion 196 of the multi-pitch coil 186 may also be seen in FIG. 10.

Referring now most particularly to FIGS. 11-16, further details of a possible construction for the bendable stiffening member 184 are provided. FIG. 11 is an isometric view of the bendable stiffening member 184. In this embodiment, a multi-pitch coil 186 is mounted within a bendable coil support tube 188. FIG. 12 depicts one type of multi-pitch coil 186 that could be assembled in the coil support tube 188. The multi-pitch coil 186 depicted in FIG. 12 includes two spaced-coil portions 194, two stacked-coil portions 196, and a centrally-located, spread-coil portion 198 (see also FIG. 14). In one embodiment, each spaced-coil portion 194 comprises a plurality (e.g., six) of slightly separated, individual coils 200; and each stacked-coil portion 196 comprises a plurality (e.g., thirty-two) of touching, individual coils 202; and the centrally-located, spread-coil portion 198 comprises a plurality (e.g., two) of slightly separated, individual coils 204. Referring back to FIG. 11, it possible to see that the two spaced-coil portions 194 extend from the longitudinal ends of the coil support tube 188 in this embodiment. An additional advantage of this configuration is that the gaps between coils 200 permit entry of a melt-processable material into these gaps when the catheter is manufactured (e.g., during a reflow process), which can help to hold the bendable stiffening member 184 in place in the assembled catheter.

In the particular embodiment shown in FIGS. 11-16, the multi-pitch coil 186 is 0.74 inches long, each of the two stacked-coil portions 196 is 0.1 inches long, and the spread-coil portion 198 is 0.018 inches long. Further, in this embodiment, each spaced-coil portion 194 comprises six coils (0.016666 pitch), and the central, spread-coil portion comprises two coils and 0.001 gaps 206 (0.009 pitch). In an alternative embodiment, two spaced-coil portions may be separated by a single, centrally-located stacked-coil portion. In other alternative embodiments, a single pitch coil could be used, for example, a tightly wound coil having no gaps between any coils from end-to-end, or a coil having the same size gap (e.g., a 0.001 gap) between all coils.

FIGS. 13, 14, and 15, are top, front, and end views, respectively, of the multi-pitch coil 186 depicted also depicted in FIG. 12. Although a variety of coil wire dimensions may be used effectively, a coil formed with an inner diameter 208 (shown in, for example, FIG. 15) of 0.011 inches, a wire thickness 210 (see FIG. 16) of 0.005 inches, and a wire width 212 (see FIG. 16) of 0.008 inches has been found to work effectively with an appropriately-sized pull wire 40, 42. Coils having an inner diameter of 0.014 inches, a wire thickness of 0.003 inches, and a wire width of 0.008 inches; or an inner diameter of 0.014 inches, a wire thickness of 0.005 inches, and a wire width of 0.008 inches have also been found to work effectively with an appropriately-sized pull wire. By varying, for example, the location and the size of the gaps between adjacent coils, the dimensions of the wire used to form the coils, the size of the coils (e.g., ID and OD), the thickness of the coil support tube, the material from which the coil support tube is constructed, the length of the coil support tube relative to the length of the coil, and how tightly the coil support tube fits over the outer diameter of the coil, it is possible to adjust and customize the bending stiffness, the bending moment, and the bending radius of the resulting shape of the deflected catheter shaft distal portion. It should also be noted that the bendable stiffening member 184 does not carry a compression load like the compression load carried by the compression coils. It should also be noted that the bendable stiffening member 184 could comprise a single component (e.g., a flexible tube not requiring an internal spring).

In various embodiments, a catheter may comprise a flexible tip assembly, which may be positioned and/or constructed similar to tip assemblies 18 and/or 18' described above. One embodiment of a flexible tip assembly 300 is illustrated in FIG. 17. The flexible tip assembly 300 has a longitudinal axis 307 and can comprise a flexible tip electrode 301, an electrode wire 315, a stop tube 310, a fluid lumen manifold 311, and a thermal sensor 317. The flexible tip electrode 301 can comprise a tip electrode distal end 306, a proximal stem 305, a recess 329, and an electrode wall 302. The electrode wall 302 can comprise at least one linear gap 303. The at least one linear gap 303 can extend along an outer radial surface of the flexible tip electrode 301 and can form a variety of patterns on the outer radial surface of the flexible tip electrode 301. In one embodiment, the pattern is an interlocking dovetail pattern. The interlocking dovetail pattern can comprise a plurality of blocks 304 wherein each of the blocks comprises a head 332 and a neck 331 (see FIG. 18). Alternatively, the pattern can be and, in one embodiment, is any type of interlocking arrangement that provides for relative movement in the proximal and distal direction with regard to either all or part of tip assembly 108. For example, alternative patterns of the interlocking arrangement can be and, in one embodiment, is bulbous, trapezoidal, triangular, rectangular, and any other shape that creates an interlocking fit.

The electrode wire 315 is coupled to the recess 329 of the flexible tip electrode 301. The electrode wire 315 can be coupled to the flexible tip electrode 301 by soldering, adhesive, or other methods known in the art. The electrode wire 315 can be surrounded along part of its length by a wire coating 318. The wire coating 318 can electrically insulate the electrode wire 315 from other components of the catheter. The electrode wire 315 can be connected to, for example, monitoring or recording or ablation devices, such as a radiofrequency (RF) generator. The distal end of thermal sensor 317 can be positioned proximate the tip electrode distal end 306 and can be used to monitor the operating temperature of the flexible tip electrode 301 or the temperature of tissue adjacent the flexible tip electrode 301. The stop tube 310 may be coupled to the fluid lumen manifold 311 and configured to interact with a portion of the flexible tip electrode 301 to control the distance that a distal end of the fluid lumen manifold 311 can extend into the flexible tip electrode 301.

FIG. 18 illustrates the embodiment of the flexible tip assembly 300 shown in FIG. 17 rotated 90 degrees about a longitudinal axis of the flexible tip assembly 300. The electrode wire 315 and the wire coating 318 covering a portion of the electrode wire is illustrated traveling parallel to a longitudinal axis of the flexible tip assembly 300. The wiring of thermal sensor 317 is illustrated traveling parallel to the longitudinal axis of the flexible tip assembly 300 and in the illustrated configuration is offset from the electrical wire 315 by 90 degrees around the outer radial surface of the flexible tip electrode 301.

FIG. 19 shows a cross-sectional view of the embodiment illustrated in FIG. 18 taken along line 19-19. The flexible tip assembly 300 comprises the flexible tip electrode 301, a manifold assembly 319, and the thermal sensor 317. The flexible tip electrode comprises a center cavity 308, a coil 309, an electrode wall 302, a linear gap 303, a proximal stem 305, a ledge feature 320, and a proximal face 322. The coil 309 is configured to be located within the center cavity 308 of the flexible tip electrode 301 and can be configured to provide structural integrity to the flexible tip electrode and to bias the flexible tip electrode 301 into pre-determined arrangements. The coil 309 can bias the flexible tip electrode 301 in a longitudinal direction or in a pre-bent configuration. In one embodiment, the coil 309 can comprise a resilient material such as stainless steel and/or a shape memory material such as nitinol. The electrode wall 302 can comprise at least one linear gap 303. In the illustrated embodiment the at least one linear gap extends from an outer radial surface of the electrode wall 302 through an inner radial surface of the electrode wall 302. When the at least one linear gap 303 extends through the electrode wall 302 as illustrated, irrigant delivered to the flexible tip electrode 301 can pass through the electrode wall 302. The irrigant is fluidly coupled to the area surrounding the outer radial surface of the flexible tip electrode 301. The proximal stem 305 of the flexible tip electrode 301 may couple the tip assembly 300 to the deflectable catheter shaft section 12 (see FIG. 1-4) or 12' (see FIG. 5) by way of adhesive, epoxy, reflowed shaft polymer material, and/or other bonding materials or techniques. Further, the proximal stem 305 can comprise an inner surface 321, a ledge feature 320 and a proximal face 322. The inner surface 321 of the proximal stem 305 can define a lumen through which the manifold assembly can pass. The ledge feature 320 may be an annular or partially annular lip or protrusion from inner surface 321 that is sized and configured to interact with a manifold assembly, such as manifold assembly 319 illustrated here, such that the manifold assembly 319 can be inserted a predetermined distance into the center cavity 308. As noted above, the ledge feature 320 can comprise a ridge or narrowing of the inner surface 321 of the proximal stem 305. In other embodiments the ledge feature can comprise a non-continuous feature to restrict the movement of the stop tube 310 past a certain point in the proximal stem 305 of the flexible tip electrode 301. The proximal face 322 of the proximal stem 305 can be configured to be used as a bonding surface for a proximal adhesive 323. The proximal adhesive 323 can be used to couple the manifold assembly 319 to the proximal stem 305 of the flexible tip electrode 301.

Referring still to FIG. 19, the manifold assembly 319 can comprise the fluid lumen manifold 311 and the stop tube 310. The fluid lumen manifold 311 can comprise a plurality of sideholes 314 in a distal section. The plurality of sideholes 314 can be configured to deliver irrigant into the center cavity 308 in a desired manner. As a result, in some embodiments, more proximally located sideholes 314 can be larger in diameter than the sideholes 314 found more distally on the fluid lumen manifold 311. In other embodiments the more proximally located sideholes 314 can be smaller in diameter than the sideholes 314 found more distally on the fluid lumen manifold 311. In yet other embodiments the plurality of sideholes 314 can comprise the same general diameter. The stop tube 310 can be configured to couple to the fluid lumen manifold 311 through the use of adhesive or other process. The stop tube 310 can be further configured to interact with the ledge feature 320 of the proximal stem 305 to control the length the distal portion of the manifold assembly 319 is inserted into the center cavity 308 of the flexible tip electrode 301. A proximal end of the stop tube 310 can extend past the proximal face 322 of the proximal stem 305 when the stop tube 310 is butted to the ledge feature 320. The stop tube 310 can provide a ledge adjacent the proximal face 322 so that when the proximal adhesive 323 is applied to the proximal face 322 of the proximal stem 305 the stop tube 310 will keep the adhesive from an outer surface of the fluid lumen manifold 311. The stop tube 310 can be configured to provide an appropriate length so that when an adhesive is applied in a semi-liquid state, the adhesive's profile is entirely on a stop tube outer surface 348 and does not cover a proximal face of the stop tube 310 or an outer surface of a fluid lumen manifold. By keeping the adhesive away from the proximal face of the stop tube 310 the distance between the proximal face of the stop tube and other components of the flexible tip assembly can be kept to a known, consistent value. The manifold assembly 319 is further configured to couple to a fluid lumen, such as tapered fluid lumen 312. In at least one embodiment the tapered fluid lumen 312 can cover a proximal portion of the fluid lumen manifold 311 and abut the stop tube 310. While the manifold assembly 319 is depicted in the illustrated embodiment coupling to a flexible tip electrode 301, the manifold assembly disclosed herein can be used with any irrigated catheter tip. The manifold assembly 319 can be used to place a distal end of the manifold assembly 319 at a predetermined location within the tip electrode and/or to place a proximal end of the manifold assembly 319 a predetermined distance from a proximal end of the tip electrode.

FIG. 20 illustrates the circled portion of FIG. 19. As illustrated in FIG. 20, in one embodiment of the manifold assembly 319, the stop tube 310 can have an outer diameter that is slightly larger than the tapered fluid lumen 312 and can be configured to provide a step feature 313 whereby a location sensor, such as a location sensor coil 350 (see FIG. 22) or other electronic sensor, can be placed a controlled and known distance from the proximal face 322 of the flexible tip electrode 301. By placing the location sensor a known distance from the proximal face 322 of the flexible tip electrode 301 a more accurate placement or registration of the location sensor can determined whereby the longitudinal axis of the sensor (FIG. 22) is coaxial or nearly coaxial with the longitudinal axis 307 of the tip assembly 300 (see FIG. 17) to allow for more accurate tip assembly position determination than may be possible if the location sensor is not coaxially aligned with the tip assembly.

Figure 21:
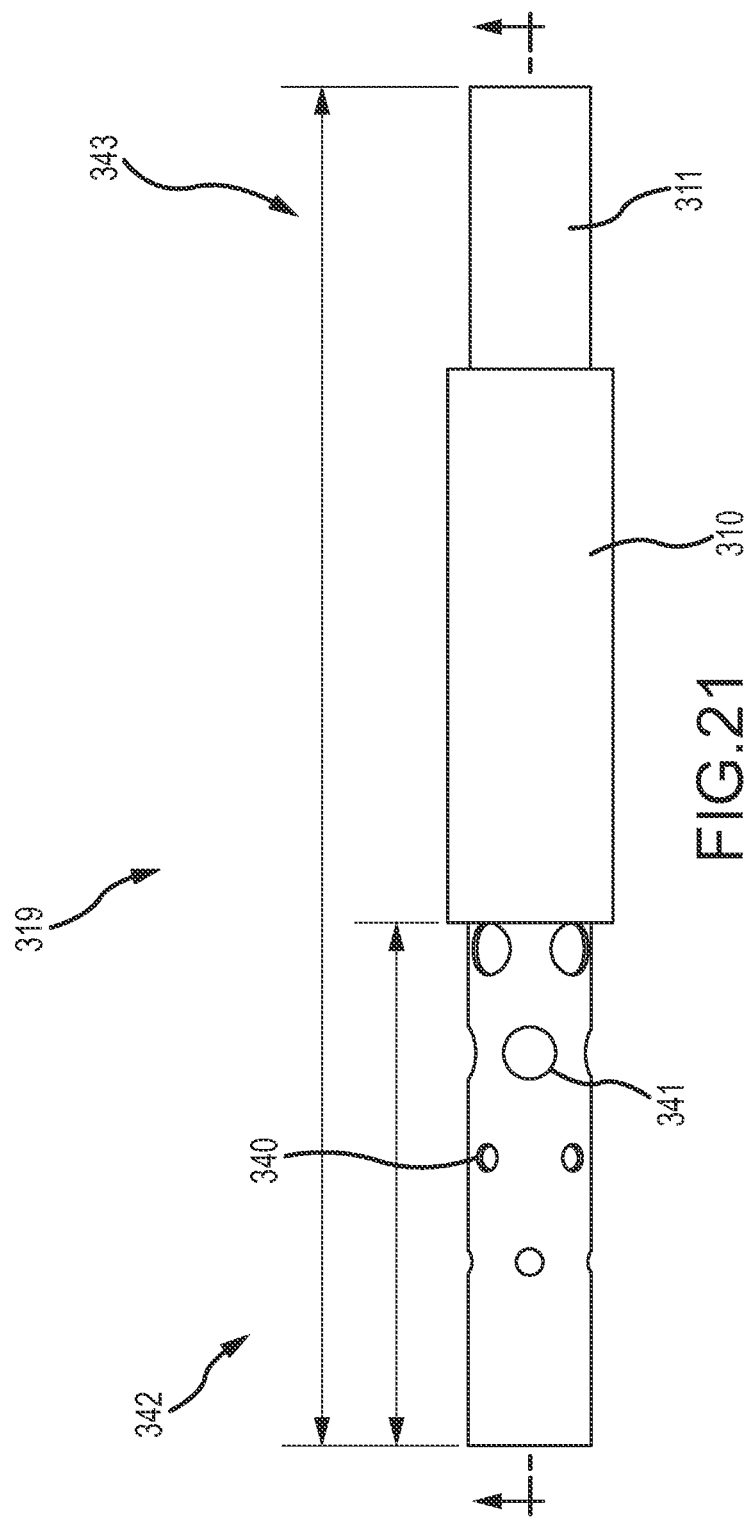
FIG. 21 is a side view of a manifold assembly in accordance with an embodiment.

FIG. 21 illustrates an enlarged view of the manifold assembly 319 shown in FIGS. 17-20. The stop tube 310 can be seen covering a middle portion of the fluid lumen manifold 311 and leaving a proximal portion 343 and a distal portion 342 of the fluid lumen manifold 311 uncovered. The distal portion 342 of the fluid lumen manifold 311 comprises a plurality of sideholes 314. In the illustrated embodiment the plurality of sideholes 314 comprise a set of 8 more proximally set sideholes 314 at a first diameter and a set of 8 more distally set sideholes 314 at a second, smaller diameter.

Figure 22:
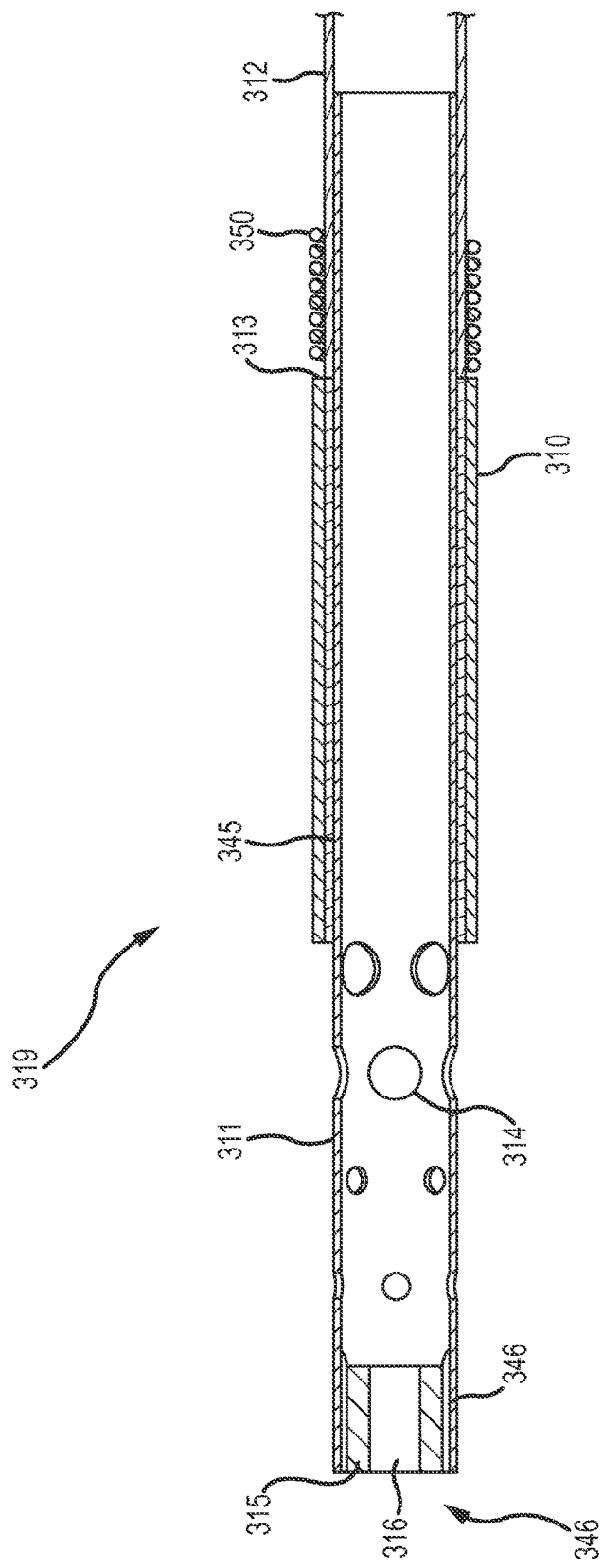
FIG. 22 is a cross-sectional view of the manifold assembly of FIG. 21 taken along line 22-22, and also including a sensor coil and a portion of a fluid lumen.

FIG. 22 depicts a cross-section of an embodiment a manifold assembly 319. The manifold assembly 319 is shown coupled to a tapered fluid lumen 312 and a location sensor coil 350. The manifold assembly 319 comprises a fluid lumen manifold 311, a stop tube 310, a stop tube adhesive 345, a plurality of sideholes 314, a lumen cap 315, and a lumen cap adhesive 346. In the illustrated embodiment, the plurality of sideholes 314 form a series of rows extending in a distal direction of the fluid lumen manifold 311. As seen in FIG. 22 the sideholes 314 in each row are offset from the sideholes 314 in the adjacent rows. The lumen cap 315 is set in a distal end 346 of the fluid lumen manifold 311. In the illustrated embodiment the lumen cap 315 is coupled to the fluid lumen manifold 311 by the lumen cap adhesive 346. The lumen cap 315 comprises a distal port 316 that can be sized to achieve a desired flow rate therethrough. In various embodiments, the distal port 316 can vary in size according to the desired fluid flow therethrough. In one embodiment, the distal port is plugged so that no fluid can flow through the distal port. The plug in the distal port can be integral to the distal port or can be a distinct plug that is coupled to the distal port. The plug can be secured to the distal port through adhesive or other bonding as is known in the art. The stop tube 310 can be coupled to the fluid lumen manifold 311 by a stop tube adhesive 345. In the illustrated embodiment a tapered fluid lumen 312 is coupled to the manifold assembly 319 such that a step feature 313 is formed at a junction of a distal end of the tapered fluid lumen and a proximal end of the stop tube 310. The step feature 313 can allow the placement of a location sensor coil 350 at a predetermined distance from a distal end of the stop tube 310, by sliding the location sensor coil 350 up to the step feature 313.

Figure 23:
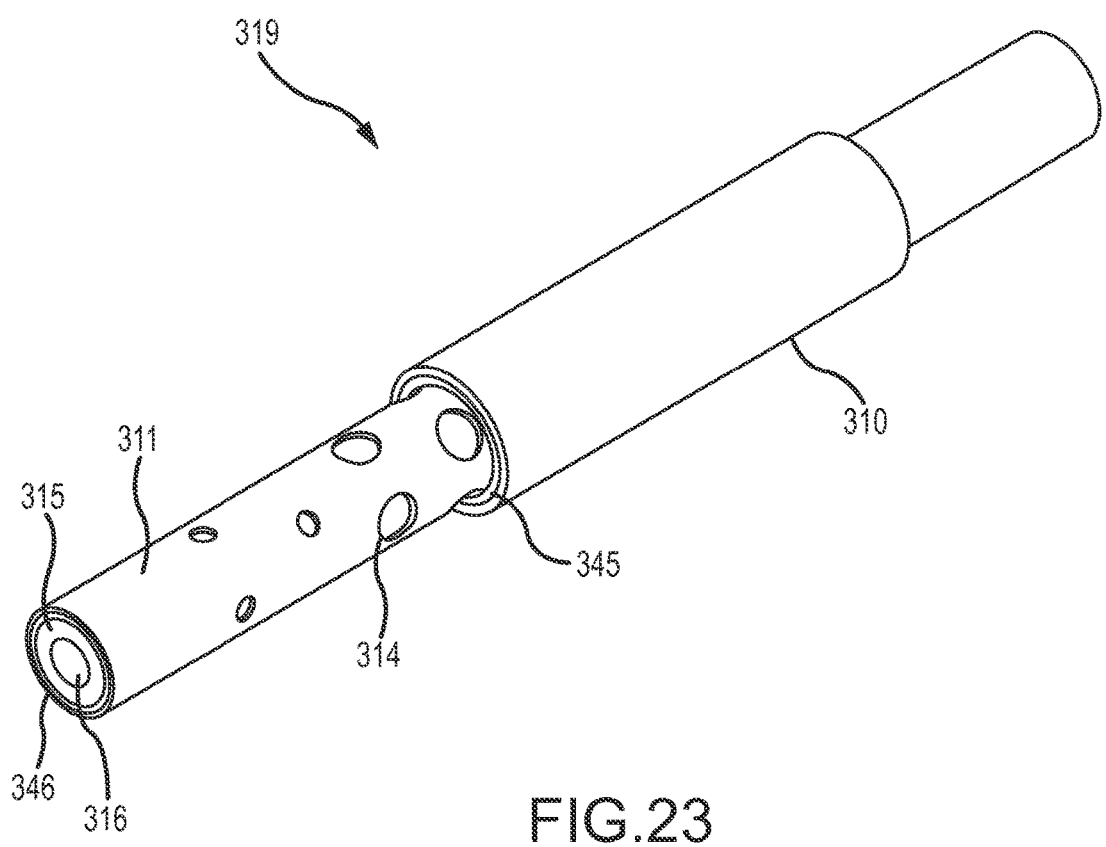
FIG. 23 is an isometric view of the manifold assembly depicted in FIG. 21.

FIG. 23 depicts an isometric view of the embodiment of a manifold assembly 319 depicted in FIG. 22. The manifold assembly 319 comprises the fluid lumen manifold 311, the stop tube 310, the stop tube adhesive 345, the plurality of sideholes 314, the lumen cap 315, and the lumen cap adhesive 346. The distal port 316 of the lumen cap 315 is also depicted.

Figure 24:
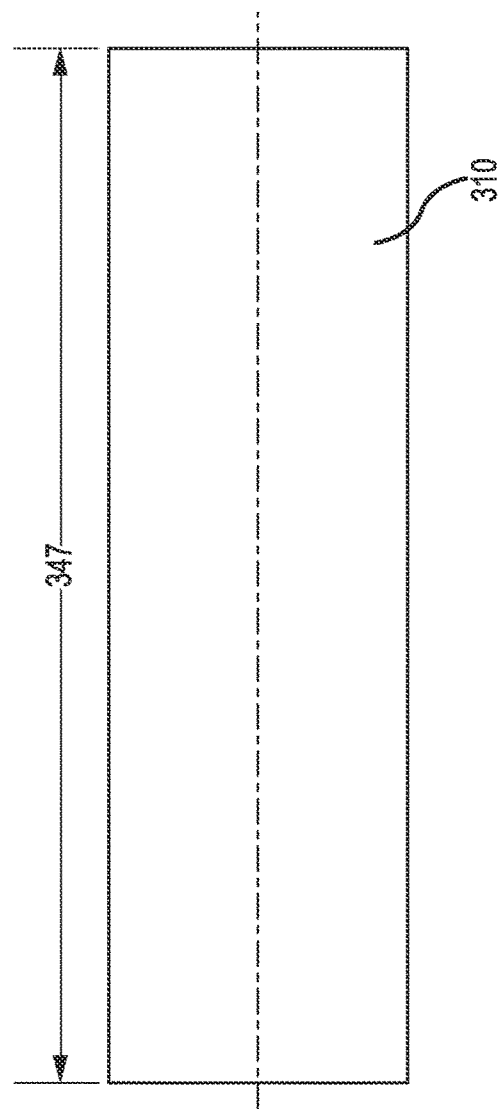
FIG. 24 is a side view of a stop tube in accordance with an embodiment.
Figure 25:
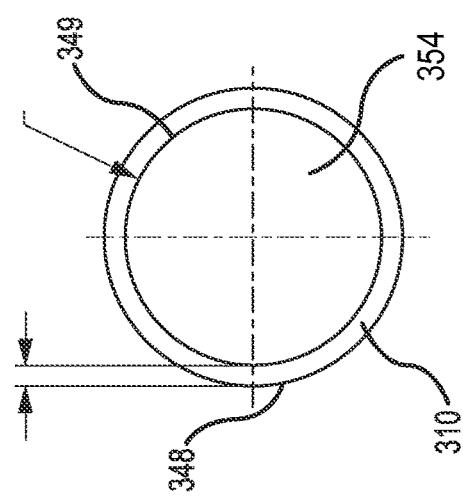
FIG. 25 is an end view of the stop tube depicted in FIG. 24.

FIGS. 24 and 25 illustrate a longitudinal side view and an end view of a stop tube 310 according to the disclosure. In one embodiment the stop tube 310 can have a length 347 of about 0.075 to 0.125 inches. In another embodiment the stop tube 310 can have a length 347 of about 0.090 to 0.115 inches. In yet another embodiment the stop tube 310 can have a length 347 of about 0.100 to 0.112 inches. The stop tube 310 can have other lengths for other embodiments. The stop tube 310 can comprise a stop tube lumen 354 and a stop tube inner surface 321. The stop tube lumen 354 can be sized and configured to fit over a fluid lumen manifold. As discussed above, the stop tube inner surface 321 can be configured to bond to said fluid lumen manifold through the use of an adhesive or other bonding process.

Figure 26:
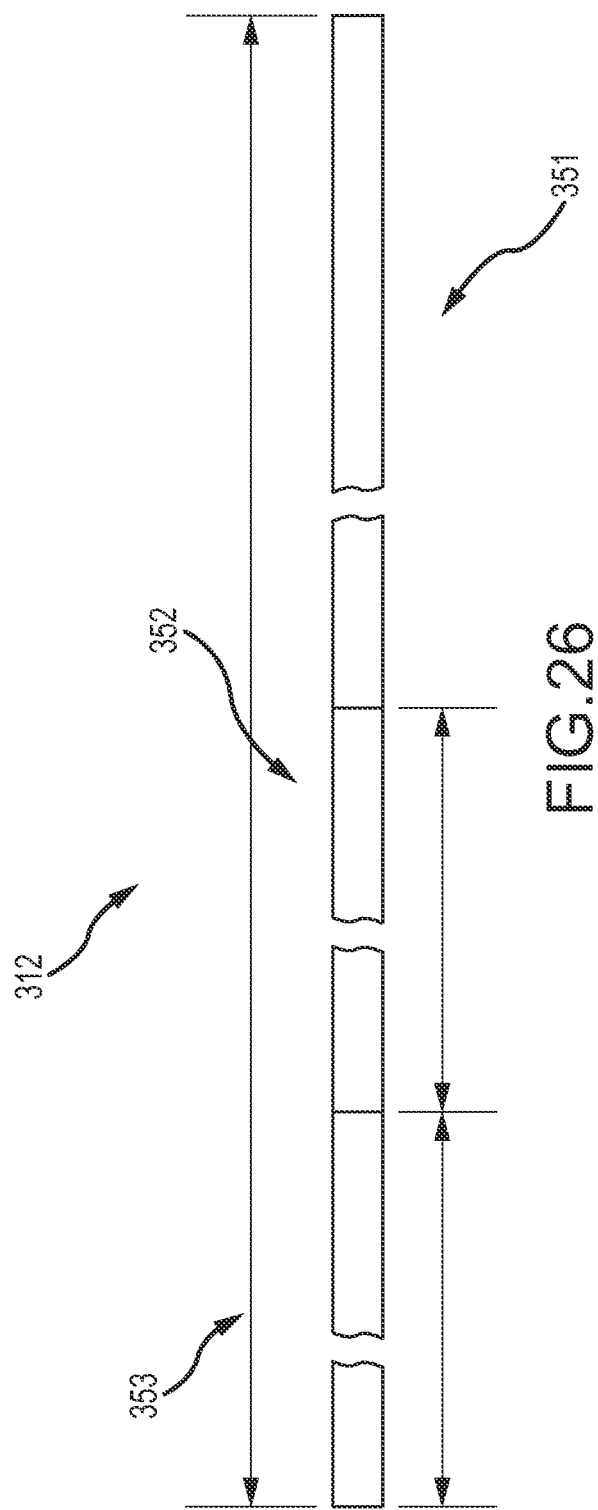
FIG. 26 is a side view of a tapered fluid lumen, with portions cut-out for clarity in accordance with an embodiment.

FIG. 26 depicts a longitudinal side view of an embodiment of a tapered fluid lumen 312. The tapered fluid lumen 312 comprises a proximal region 351 with a first outer diameter, a distal region 353 with a second outer diameter, and a tapered transition region 352. In one embodiment the diameter of the distal region 353 can be larger than the diameter of the proximal region 351. The tapered transition region 352 comprises an area where the diameter of the tapered fluid lumen 312 changes from the larger to the smaller diameter. In one embodiment, the distal region 353 of the tapered fluid lumen 312 can be configured to surround and couple to a proximal portion of a fluid lumen manifold.

Figure 29:
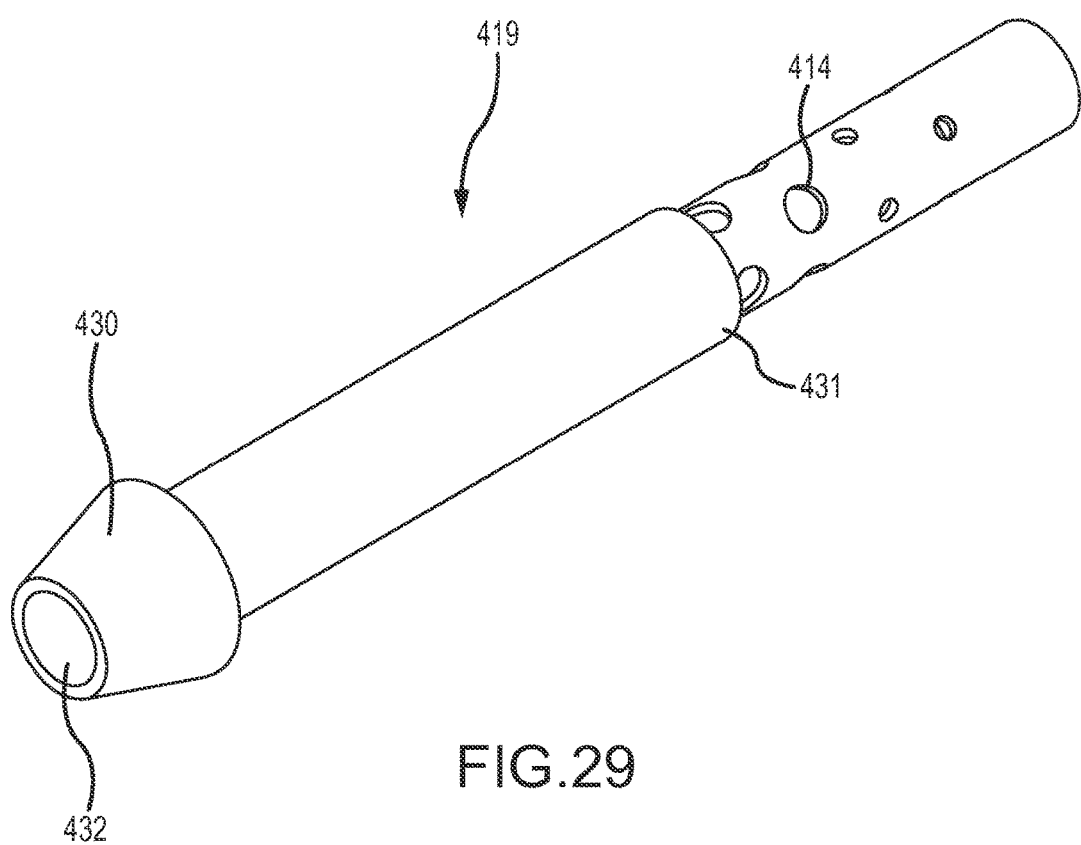
FIG. 29 is an isometric view of the manifold assembly depicted in FIGS. 27 and 28.

FIGS. 27-29 illustrate various views of another embodiment of a manifold assembly 419. The manifold assembly 419 in the illustrated embodiment comprises a barbed connector 430, a stop shoulder 431, a lumen cap 415, a distal port 416, and a plurality of sideholes 414. The sideholes 414 can vary in size. In the illustrated embodiment, a proximal set of the sideholes 414 is larger than a distal set of the sideholes 414. The lumen cap 415 comprises a distal port 416 that can provide back flow and/or back pressure during irrigant (e.g. water or saline) delivery from an inner lumen 432 through the sideholes 414 and/or the distal port 416. Some or all of the manifold assembly 419 can be made of stainless steel by a machining process and then passivated, including the sideholes 414, which may also be drilled first then passivated to remove iron oxide. By machining the manifold assembly 419 of the current embodiment in a single piece the manufacture of the manifold assembly 419 can reduce the variability in the completed manifold assembly 419. In various embodiments, a fluid (or water) deliver tube extending through at least a portion of an elongated catheter body, such as the elongated body of the deflectable catheter shaft section 12 (see FIG. 1-4) or 12' (see FIGS. 5 and 6), and/or intermediate catheter shaft section 164 (see FIGS. 5 and 6), and/or proximal catheter shaft section 20 (see FIG. 1), and made of a flexible, elastic, stretchable polymer such as a thermoplastic urethane ("TPU", which may be available under the brand names PELLETHANE or ESTANE, both from The Lubrizol Corporation, Wickliffe, Ohio, USA) may be stretched over a barbed connector 430 of the manifold assembly 419 to form a complementary pocket, such as pocket 187 seen in FIG. 6. A stop shoulder 431 of the manifold assembly 419 may abut a ledge feature of the flexible tip electrode of the tip assembly 300 discussed above (see FIG. 17) such that irrigation fluid may be delivered from sideholes 414 into an inner cavity of the flexible tip electrode and ultimately out of the electrode through at least one exterior port or gap of an outer wall of the electrode.

Figure 32:
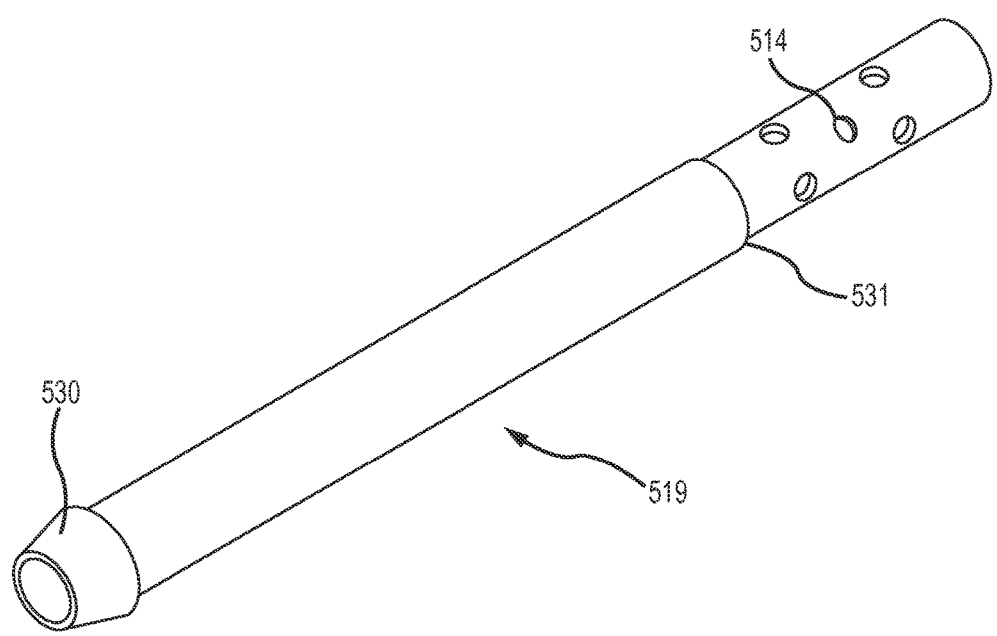
FIG. 32 is an isometric view of the manifold assembly depicted in FIGS. 30 and 31.

FIGS. 30-32 illustrate several views of another embodiment of a manifold assembly 519. In the illustrated embodiment, the manifold assembly 519 comprises a barbed connector 530, a stop shoulder 531, a lumen cap 515, a distal port 516, and a plurality of sideholes 514. The sideholes 514 of the illustrated embodiment can comprise a consistent size and no distal constriction around a distal port 516.

Figure 33:
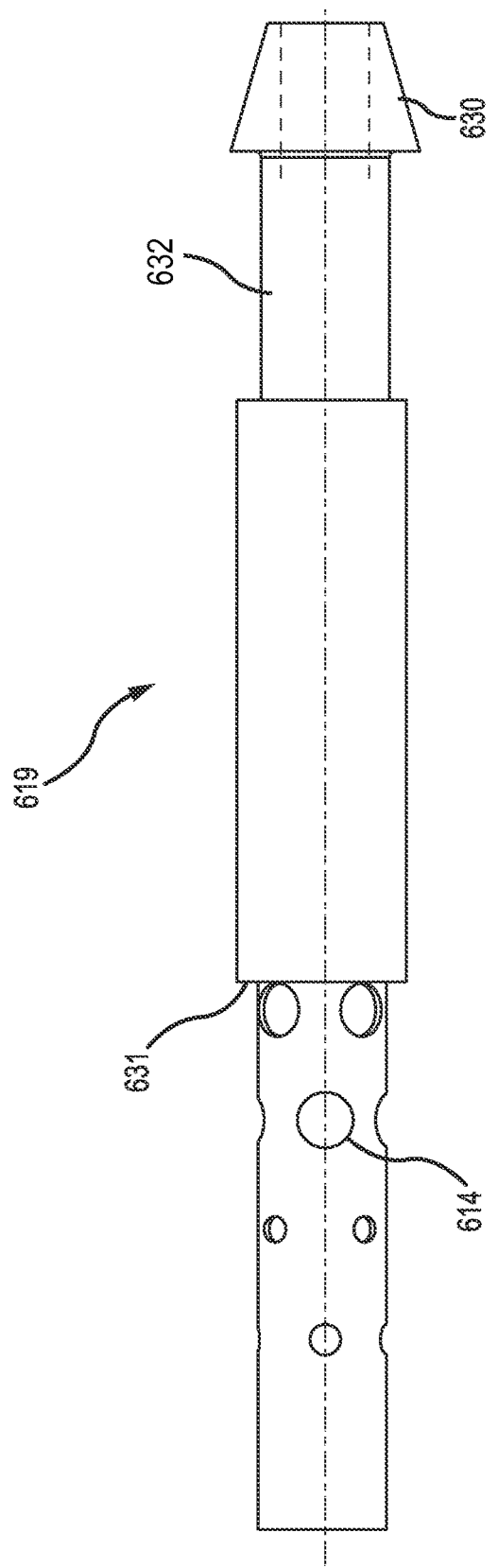
FIG. 33 is a side view of a manifold assembly in accordance with an embodiment.

FIG. 33 illustrates yet another embodiment of a manifold assembly 619 according to the disclosure. The manifold assembly 619 can comprise a barbed connector 630, a sensor depression 632, a stop shoulder 631, and a plurality of sideholes 614. The sensor depression 632 can be sized and configured to couple to a location sensor coil 350 (see FIG. 22). The manifold assembly 619 can be manufactured from stainless steel, PEEK or the other suitable. When the manifold assembly 619 is made of PEEK or the like less interference can occur when using a location sensor coil.

Although at least one embodiment of a manifold assembly have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter tip assembly comprising:
   a tip electrode comprising, an electrode wall, a ledge feature and a center cavity, wherein the electrode wall defines the center cavity; and
   a manifold assembly comprising a fluid lumen manifold and a stop tube, wherein a distal portion of the fluid lumen manifold further comprises a plurality of sideholes, and wherein a distal end of the manifold assembly is disposed within the center cavity, wherein the stop tube is coupled to the fluid lumen manifold and abuts the ledge feature such that a distal end of the fluid lumen manifold extends a pre-determined distance into the center cavity of the tip electrode, and wherein the pre-determined distance is configured to allow an irrigation fluid through the plurality of sideholes into the center cavity of the tip electrode.

2. The catheter tip assembly according to claim 1 further comprising a thermal sensor coupled to the tip electrode.

3. The catheter tip assembly according to claim 1 further comprising a stem including a proximal face, wherein the stop tube is coupled to the fluid lumen manifold by an adhesive positioned between the stop tube and the proximal face.

4. The catheter tip assembly according to claim 1 further comprising a location sensor adjacent the stop tube.

5. The catheter tip assembly according to claim 1 wherein the plurality of sideholes are of varying sizes.

6. The catheter tip assembly according to claim 5 wherein a subset of the plurality of sideholes more distally located comprise a smaller diameter than a subset of the plurality of sideholes more proximally located.

7. The catheter tip assembly according to claim 1 further comprising a lumen cap coupled to a distal end of the fluid lumen manifold.

8. The catheter tip assembly according to claim 7 wherein the lumen cap comprises a distal port.

9. The catheter tip assembly according to claim 1 wherein the tip electrode comprises a flexible tip electrode.

10. The catheter tip assembly according to claim 9 wherein the flexible tip electrode comprises an electrode wall, a coil, a linear gap, and a proximal stem.

11. A catheter comprising:
    a tip electrode comprising, an electrode wall, a ledge feature and a center cavity, wherein the electrode wall defines the center cavity; and
    a manifold assembly comprising a stop shoulder and a plurality of sideholes, wherein a distal end of the manifold assembly is disposed within the center cavity, wherein the manifold assembly is configured to abut the ledge feature such that a distal end of the manifold assembly extends a pre-determined distance into the center cavity of the tip electrode, and wherein the pre-determined distance is configured to allow an irrigation fluid through the plurality of sideholes into the center cavity of the tip electrode.

12. The catheter according to claim 11 wherein the manifold assembly further comprises a sensor depression.

13. The catheter according to claim 11 wherein the sensor depression is sized and configured to couple to a location sensor.

14. The catheter according to claim 11 further comprising a catheter body coupled to the tip electrode.

15. The catheter according to claim 11 wherein the manifold assembly further comprises a barbed connector.

16. The catheter according to claim 11 further comprising a deflectable catheter shaft section coupled to the tip electrode.

17. The catheter according to claim 16 wherein the deflectable catheter shaft section comprises an elongated body extending along a longitudinal axis and comprising a distal end and a proximal end; and a plurality of lumens extending along the longitudinal axis of the elongated body, wherein at least one of the plurality of lumens is abutting at least another one of the plurality of lumens.

18. A flexible tip electrode comprising:
- an electrode wall, a linear gap, a proximal stem, a ledge feature, and a proximal face, wherein the electrode wall defines a center cavity; and
- a manifold assembly comprising a fluid lumen manifold and a stop tube, wherein a distal portion of the fluid lumen manifold further comprises a plurality of sideholes, and wherein a distal end of the manifold assembly is disposed within the center cavity,
- wherein the manifold assembly is configured to engage with the ledge feature such that a proximal end of the stop tube is a predetermined distance from the proximal face of the flexible tip electrode, and wherein the pre-determined distance is configured to allow an irrigation fluid through the plurality of sideholes into the center cavity of the tip electrode.

19. The flexible tip electrode according to claim 18 further comprising a fluid lumen configured to couple to the fluid lumen manifold and abut the stop tube.

\* \* \* \* \*